United States Patent [19]

Tsien et al.

[11] Patent Number: 5,693,521
[45] Date of Patent: Dec. 2, 1997

[54] MEMBRANE-PERMEANT SECOND MESSENGERS

[75] Inventors: Roger Y. Tsien; Carsten Schultz, both of La Jolla, Calif.

[73] Assignee: The Regents of the University of California, Oakland, Calif.

[21] Appl. No.: 45,585

[22] Filed: Apr. 9, 1993

[51] Int. Cl.$^6$ .......... A61K 31/70; C07H 19/167; C07H 19/20; C12N 5/00

[52] U.S. Cl. .......... 435/240.1; 514/45; 514/47; 514/48; 435/7.21; 435/240.2; 536/26.7; 536/26.71; 536/26.72; 536/27.3; 536/117

[58] Field of Search .......... 514/47, 48, 45, 514/75, 25, 102, 103, 104; 536/1.11, 4.1, 26.7, 26.71, 26.72, 27.3, 117; 435/7.21, 240.1, 240.2

[56] References Cited

PUBLICATIONS

Abstract Form For: American Gastroenterological Association and American Association for the Study of Liver Diseases: Title—"Synergistic Epithelial Chloride Secretion Via cAMP and Calcium Patheways—A Re–Examination,"—May 10, 1992.

Abstract Form For: American Gastroenterological Association and American Association for the Study of Liver Diseases: Title—"A Possible Role for Inositol Tetrakisphosphate as a Negative Regulator of Calcium–Related Epithelial Chloride Secretion,"—May 10, 1992.

Abstract Form For: 8th International Conference on Second Messengers & Phosphoproteins: Title—"Membrane–Permeant Acetoxymethyl Esters of Inositol Phosphates: Effects on Ref–52 Fibroblasts, Pancreatic Acinar Cells, and T$_{84}$ Cells,"—Aug. 3, 1992.

Carsten Schultz, Mana Vajanaphanich, Alec T. Harootunian, Paul J. Sammak, Kim E. Barrett, and Roger Y. Tsien; "Acetoxymethyl Esters of Phosphates, Enhancement of the Permeability and Potency of cAMP," Journ. of Biol. Chem.: vol. 268: Mar. 25, 1993, No. 9: pp. 6316–6322.

Devendra N. Srivastva and David Farquhar; "Bioversible Phosphate Protective Grups: Synthesis and Stability of Model Acyloxymethyl Phosphates," Bioorganic Chemistry (1984): vol. 12: pp. 118–129.

Radhakrishnan P. Iyer, Lawrence R. Phillips, Jane A. Biddle, Dhiren R. Thakker, William Egan, Shizuko Aoki and Hiroaki Mitsuya; "Synthesis of Acyloxyalkyl Acyllplhosphonates as Potential Prodrugs of the Antiviral, Trisodium Phosphonoformate (Foscarnet Sodium)," Tetrahedron Letters (1989), vol. 30, No. 51, pp. 7141–7144.

1992 FASEB—Abstract Form: Membrane–Permanent Derivatives of Inositol Polyphosphates Applied to Ref–52 Fibroblasts—Apr. 9, 1992.

M. Berridge et al. nature, vol. 341 (21 Sep. '89) pp. 197–205.

M. Comb et al. Nature, vol. 323 (25 Sep. '86) pp. 353–356.

L. Cantley et al. Cell, vol. 64 (25 Jan. '91) pp. 281–302.

Tsien, Am. J. Physiol., vol. 32, #4 (1992) pp. C723–C728.

M. Saba et al. Life Sciences, vol. 47 ('90) pp. 307–311.

F. Guadagni et al. Int. J. Cancer, vol. 48 ('91) pp. 413–422.

R. Saperstein et al. Biochemistry, vol. 28 ('89) pp. 5694–5701.

S. B. Shears Biochem. J., vol. 260 ('89) pp. 313–324.

C. Shultz et al. FASEB J., vol. 6, #5 (Feb. 28, 1992) p. A1924 (Abstract).

K. Wenzel–Seifert et al. Naunyn–Schmiedeberg's Arch. Pharmacol., vol. 344 ('91) pp. 396–402.

D. Farquhar et al. J. Pharmaceutical Sci., vol. 72, #3 (1983) pp. 324–325.

J. Freed et al. Biochemical Pharmacology, vol. 38, #19 ('89) pp. 3193–3198.

*Primary Examiner*—Charles C. P. Rories
*Attorney, Agent, or Firm*—Oppenheimer Poms Smith

[57] ABSTRACT

Acyloxyalkyl esters of phosphate-containing second messengers which are capable of permeating cell membranes. Once inside the cell, the ester derivatives undergo enzymatic conversion to the biologically active form of the second messenger. Acyloxyalkyl esters of second messengers, such as cAMP, cGMP, inositol triphosphate and inositol tetraphosphate are disclosed.

10 Claims, 13 Drawing Sheets

Chloride secretion in response to cell permeant cAMP-derivatives.
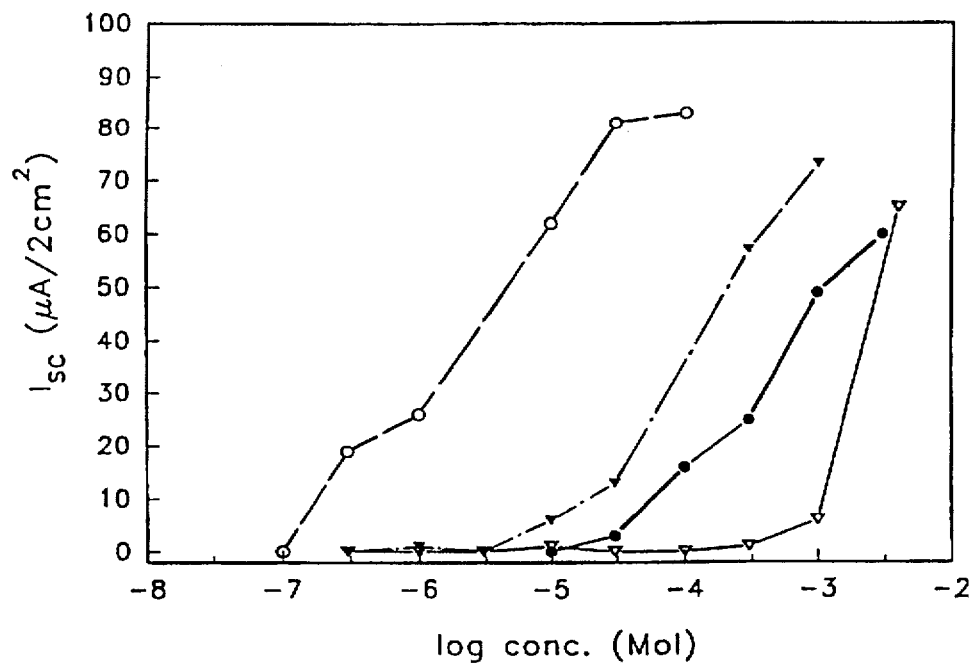
Dose-response relations for Bt$_2$cAMP/AM (○) vs Bt$_2$cAMP (●),
Fig. 2B.    8-Br-cAMP (△) and 8-pCPT-cAMP (▲).
Fig. 3A.
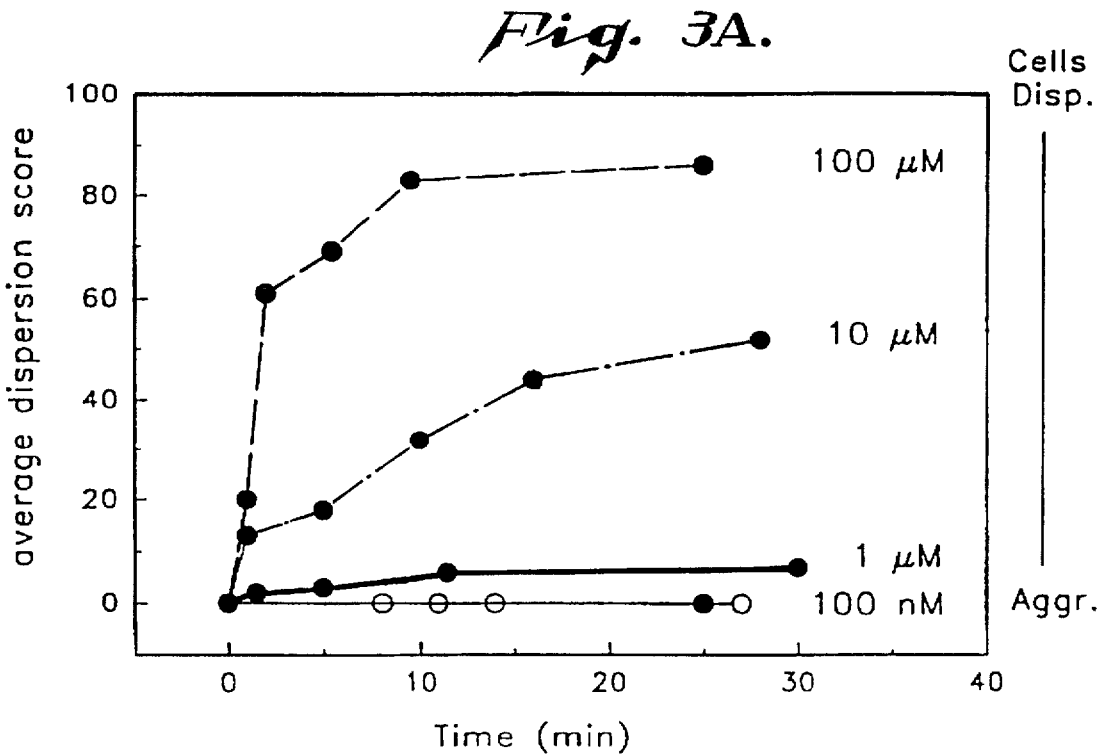

cAMP/AM

MEMBRANE-PERMEANT SECOND MESSENGERS

BACKGROUND OF THE INVENTION

This invention was made with Government support under Grant No. NS-27177, awarded by the National Institute of Health. The Government has certain rights in this invention.

1. Field of the Invention

The present invention relates generally to biologically important phosphates such as second messengers. More particularly, the present invention relates to modifying second messengers to form derivatives which can be introduced into a cell without disrupting the cell membrane. Once inside the cell, the derivative is converted back to the biologically active second messenger.

2. Description of Related Art

The publications and other reference materials referred to herein to describe the background of the invention and to provide additional detail regarding its practice are hereby incorporated by reference. For convenience, the reference materials are numerically reference and grouped in the appended bibliography.

Second messengers are ions or small molecules that carry information from the cell membrane to targets on the inside of the cell. They play a major role in biological signal transduction and amplification (1). A common feature of most of the known second messengers, such as adenosine 3',5'-cyclic monophosphate (cAMP) (2,3), guanosine 3',5'-cyclic monophosphate (4) (cGMP), myo-inositol-1,4,5-trisphosphate (1,4,5)IP$_3$) or myo-inositol-1,3,4,5-tetrakisphosphate (1,3,4,5)IP$_4$) (5), is the presence of phosphates. The correct number and position of these phosphates is essential for biological specificity and also confers extreme hydrophilicity (6,7).

The hydrophilicity of second messengers prevents endogenously generated molecules from leaking out of cells. As a result, high sensitivity is maintained within the responding cell and freedom from cross-talk between neighboring cells is achieved. However, the membrane impermeability of second messengers also makes deliberate extracellular application difficult or ineffective (2,6,8), even though such intervention would often be very useful for research or therapeutic reasons.

One approach for introducing phosphate containing compounds into cells involves using protective groups to reversibly convert the negatively charged phosphate compound into a neutral compound for transport through the cell membrane. The protective group is chosen so that it is enzymatically cleaved from the phosphate compound inside the cell to produce the original phosphate compound. For example, lipophilic, intracellularly hydrolyzable derivatives have been useful for amine, hydroxyl, and carboxylate moieties (9–12). Acetoxymethyl (AM) esters of polycarboxylate cation indicators and chelators are have also been used (12–14). Analogous acyloxyalkyl esters applied to phosphates are known, but they have been less widely exploited (15).

On simple model phosphates, uses of AM esters have been limited to potential therapeutic drugs, such as phosphonoformate (foscarnet) (16), antiviral nucleotides such as 5-fluoro-2'-deoxyuridine monophosphate (17,18), and a 3-phosphonate-containing inhibitor of the insulin receptor kinase (19). The phosphonoformate esters proved not to be biologically useful due to failure to hydrolyze to the correct products (16), but esterification was found to enhance the effectiveness of the antiviral nucleotides and kinase inhibitor (17–19).

Considerable work has been done on o-nitrobenzyl esters as photolyzable ("caged") derivatives of ATP (20), cyclic nucleotides (21,22), and inositol phosphates (23). However, the emphasis has been on producing a kinetically fast and complete transition from a monoester to the active freed phosphate metabolite (24,25), rather than as a general means of achieving membrane permeability. In addition, nitrobenzyl esters become cumbersome if more than one are required to mask negative charges, because multiple groups add considerable bulk and require high doses of UV to cause cleavage of all the groups.

Although numerous different myo-inositol polyphosphates are possible, only about a dozen have been found in cells. Their intracellular functions are controversial or unknown, except for myo-inositol 1,4,5-trisphosphate (IP$_3$), whose role as an intracellular second messenger to release Ca$^{2+}$ from internal stores is unquestioned (26). The next most studied inositol polyphosphate is myo-inositol 1,3,4,5-tetrakisphosphate (IP$_4$), which is believed to cooperate with IP$_3$ to open Ca$^{2+}$-channels in the plasma membrane (27–30) or to resequester Ca$^{2+}$ released by IP$_3$ (31, 32). However, these hypotheses remain controversial (33–37).

Almost nothing is known about intracellular functions for other inositol polyphosphates. Detailed dissection of the roles of inositol polyphosphates is often difficult if they are endogenously generated in response to agonists, since such stimulation may affect multiple receptors, G proteins, diacylglycerol formation, multiple inositol polyphosphates, and yet other transduction pathways. Direct introduction of specific inositol polyphosphates is often preferable.

The high negative charge of inositol polyphosphates results in negligible passive permeability through membranes. Existing methods for introducing inositol phosphates include microinjection, patch-clamp techniques, and permeabilization by electroporation, detergents like saponin, or removal of extracellular Ca$^{2+}$. All these methods breach the plasma membrane and jeopardize the more complex functions and long-term viability of the cells. Furthermore, microinjection and patch techniques can only be applied to a few cells at a time.

In view of the above, there is a need to provide a procedure for increasing the membrane permeability of second messengers so that they can be introduced effectively into cells in amounts which are useful for investigational or therapeutic purposes.

SUMMARY OF THE INVENTION

In accordance with the present invention, compositions and methods are provided for increasing the permeability of phosphate-containing second messengers into a cell without disrupting the cell membrane. The invention involves esterifying the phosphate groups present in the second messenger molecule to form an acyloxyalkyl ester derivative. The acyloxyalkyl ester of the second messenger has a neutral charge and therefor can permeate into the cell without disrupting the cell membrane. Once inside the cell, the esters are cleaved to convert the molecule back to its biologically active form. Acetoxymethyl esters were found to provide optimum charge neutralization while still being easily cleaved by cell enzymes.

As a further feature of the present invention, hydroxyl groups which are present in the second messenger molecule are masked to aid in synthesis of the derivatives and further enhance the permeability of the second messenger derivative into the cell. The hydroxyl groups are masked with an acyl group which can be easily cleaved once the modified second messenger enters the cell. Butyryl groups were found to provide optimum masking while still being easily cleaved by cell enzymes.

As one aspect of the present invention, the phosphate and hydroxy groups of cyclic nucleotides, such as cAMP and cGMP, are esterified and acylated to form neutral derivatives. These neutral derivatives were found to cross the cell membrane and to be converted into their active form once inside the cell. The introduction of cAMP and/or cGMP into a cell is useful for both investigational and therapeutic purposes.

Another aspect of the present invention involves the esterification and acylation of second messengers such as, inositol triphosphate and inositol tetraphosphate. The resulting neutral derivatives were also found to permeate into cells and were converted back into their active forms once inside the cell. The introduction of inositol phosphates into cell is also useful for both investigational and therapeutic purposes.

As a further feature of the present invention, 8-substituted cyclic nucleotides are esterified and acylated to increase their permeability into cells. These synthetic nucleotides are useful for investigational and therapeutic purposes. The increase in permeability provided by the present invention provides a convenient procedure for introducing the 8-substituted cyclic nucleotides into cells.

The present invention also covers methods for preparing the acyloxymethyl esters where the hydroxyl groups are masked during synthesis by acylation with acyl groups having from 1–4 carbon atoms. It was found that butyryl groups provided optimum masking for synthesis and also could be easily removed enzymatically after entry into the cell.

The above described and many other features and attendant advantages of the present invention will become better understood by reference to the following description when taken in conjunction with the accompanying drawings.

BRIEF DESCRIPTION OF THE DRAWINGS

FIG. 2B is a graph showing a comparison of chloride secretion initiated by $Bt_2cAMP/AM$ and other derivatives.

FIG. 3A shows the results of tests demonstrating the ability of $Bt_2cAMP/AM$ to disperse fish dermal chromatophores.

DESCRIPTION OF THE PREFERRED EMBODIMENTS

Figure 1:
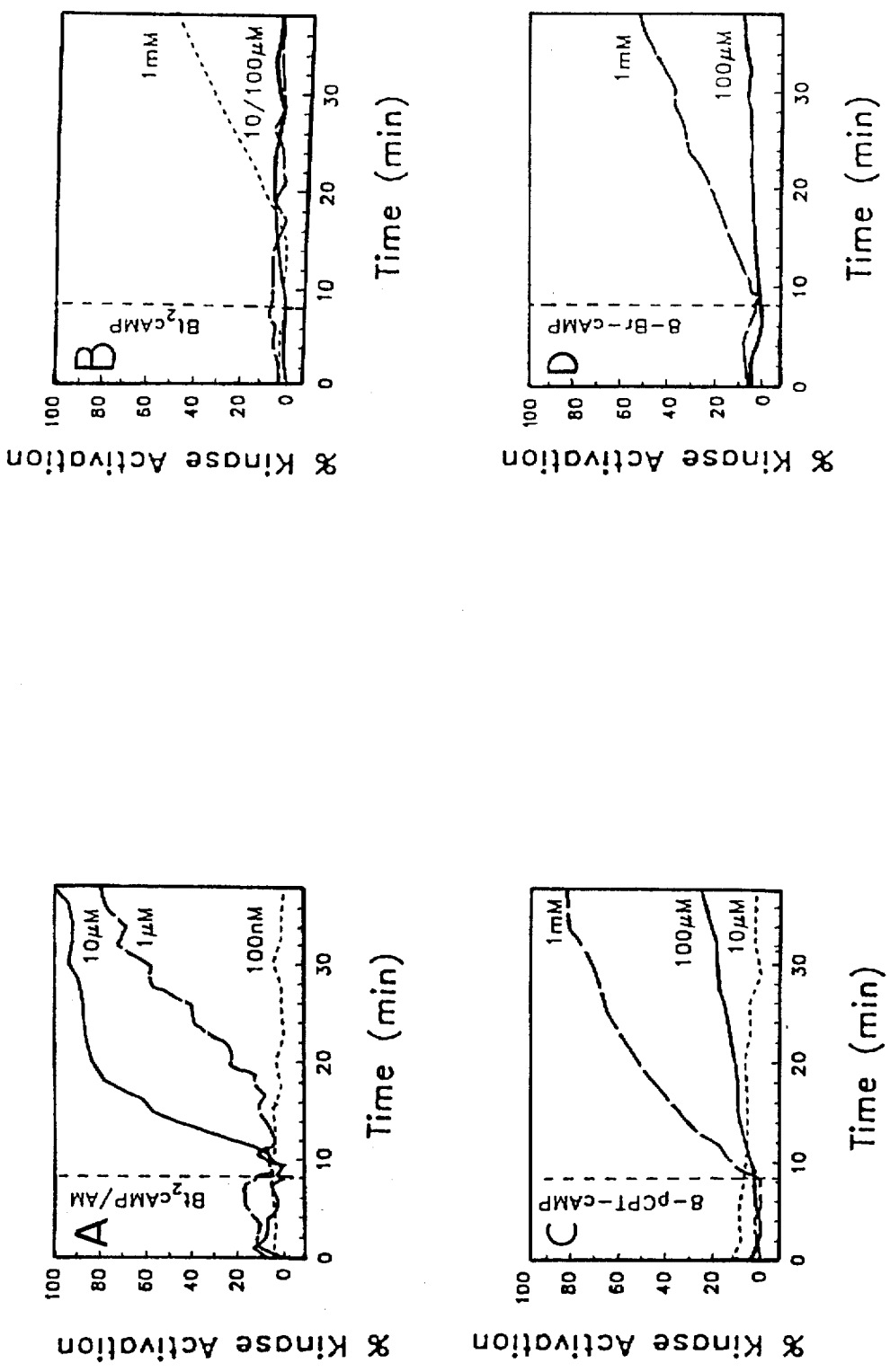
FIGS. 1A–1D are four graphic representations of the results of tests showing the kinase activation capability of $Bt_2cAMP/AM$ in comparison to other derivatives.

The present invention is directed to modifying second messengers and derivatives thereof which contain phosphates so that they can be easily introduced into a cell without disrupting the cell membrane. The invention involves esterifying the phosphate groups present in the second messenger to form a neutral acyloxyalkyl derivative which can readily diffuse through the cell membrane. The acyl group may contain up to 5 carbon atoms and is located at the 1 position of the alkyl group. The alkyl group may contain up to 7 carbon atoms. It was found that acetoxymethyl esters provide optimum cell membrane transport while still being amendable to cleavage from the second messenger after entry into the cell. For second messengers having multiple phosphate groups, it is preferred that all of phosphate groups be masked as acetoxymethyl esters.

The present invention is applicable to increasing the cell permeability of a wide variety of phosphate-containing second messengers and derivatives thereof. Preferred exemplary phosphate-containing second messengers include cAMP, cGMP, 1,4,5 $IP_3$, 1,3,4,5 $IP_4$ and myo-inositol 1,4, 5,6-tetrakisphosphate. The present invention is also applicable to derivatives of second messengers. Exemplary derivatives include the 8-substituted derivatives of cAMP or cGMP. The 8-substituted derivatives include 8-bromo-cAMP or cGMP, 8-chloro-cAMP or cGMP and 8-para-chlorophenylthio (cCPT) cAMP or cGMP.

The following description will be limited to forming derivatives of five second messengers which all were shown to have increased cell membrane permeability. It will be understood by those skilled in the art that the invention is not limited to the specific second messengers discussed below.

It is preferred that the hydroxyl groups of the phosphate-containing second messengers be masked or protected during synthesis. Masking with acyl groups having up to 4 carbon atoms is preferred. Larger acyl groups are not preferred because they are more difficult for the cell to cleave from the second messenger.

Examples of practice showing the synthesis and use of cAMP/cGMP acetoxymethyl esters in accordance with the present invention are as follows:

Proton and $^{31}$ P NMR spectra were obtained in $CDCl_3$, with residual $CHCl_3$ ($\delta$=7.26), being used as the internal standard for $^1H$ spectra. 85% phosphoric acid was used as an external standard for $^{31}P$ spectra. All NMR spectra were recorded on either a Varian Gemini-200 (200 MHz) or a General Electric QE-300 (300 MHz) spectrometer and are reported with the following abbreviations: s, singlet; d, doublet; t, triplet; dd, doublet of doublets; m, complex multiplet. Fast atom bombardment mass spectroscopy (with glycerol as matrix) and precise mass determinations were performed by the mass spectroscopy facility of the University of California, Riverside. Capillary electrophoresis was performed on a Dionex CES.

Pyridine and acetonitrile used in the synthesis were stored over activated molecular sieve (3 Å) for at least 3 d. All other solvents were purchased in highest purity available and were used as received. N,N-Diisopropylethylamine (DIEA) was distilled from $CaH_2$. Acetoxymethyl bromide (AM-Br) was prepared according to known procedures (38). All nucleotides were from Sigma. Phenylphosphonic acid was from Fluka, Switzerland. 4-Methylumbelliferylphosphate was from Boehringer, FRG. All other reagents were from Aldrich.

TABLE I

Structures of Acetoxymethyl Esters of Various Organic Phosphates

| comp. | Structure | counter[a] ion M⁺ | yield[b] | $^{31}$P-NMR [ppm] |
|---|---|---|---|---|
| | $\text{O=P(O^-M^+)} + \text{B-OAc} \xrightarrow{-\text{MBr}}$ | | | |
| 1 | AcO-O-P(=O)(O-)(O-aryl coumarin structure with AcO-O- group) | Ag⁺ | 72% | −9.1 |
| 2 | AcO-O-P(=O)(O-CH₂-OAc)(O-CH₂-OAc) | Ag⁺ | 98% | −2.25 |
| 3 | AcO-O-P(=O)(phenyl)(O-CH₂-OAc) | HDIEA⁺ | 86% | 18.70 |
| 4a/4b | BtAde(BtGua) ribose-cyclic phosphate with AcO-O-P* and OBI | HDIEA⁺ / Ag⁺ | 59% / 52% | −8.0/[c] / −5.0 |
| 5a/5b | | HDIEA⁺ | 40% | −5.5/[c] −8.5 |

[a]M⁺ specifies the counter ion for the phosphate-containing starting material; HDIEA⁺ = diisopropylethylammonium.
[b]Yield by weight unless otherwise noted.
[c]Shift values for both diastereomers.

The compounds shown in Table 1 were synthesized as set forth below: Compounds 1–3 were synthesized for comparative purposes. Compounds 4 a/b (cAMP/AM) and 5 a/b (cGMP/AM) are preferred exemplary compounds in accordance with the present invention.

Synthesis of 4-Methylumbelliferyl Phosphate Bis(acetoxymethyl)ester (1)—The dilithium salt of 4-methylumbelliferyl phosphate (200 mg, 0.74 mmol) was dissolved in water and a concentrated solution of silver acetate was added. The disilver 4-methylumbelliferyl phosphate precipitated immediately and was filtered, washed with water and dried to a shining silver-white powder (yield: 277 mg, 79%). The silver salt (60 mg, 0.13 mmol) was suspended in 1 mL dry CH$_3$CN and 50 mg (0.33 mmol) AM-Br was added. At frequent intervals, the mixture was treated for 2 minutes at a time in an ultrasonic bath (Branson B-220). Frequent monitoring by $^1$H NMR showed the reaction to be complete after 4 h. The supernatant was evaporated to dryness to yield 38 mg (72%) of 4-methylumbelliferyl phosphate bis(acetoxymethyl)ester (1); $^1$H NMR (CDCl$_3$, 200 MHz) δ2.12 (s, 6H), 2.43 (s, 3H), 5.73 (dAB, 4H, J$_{AB}$=5.5 Hz, J$_{PH}$=14.2 Hz, —CH$_2$—), 6.27 (s, 1H, H3), 7.17–7.25 (m, 2H, H6,H8), 7.59 (m, 1H, H5); $^{31}$P NMR (CDCl$_3$, 121.5 MHz) δ−9.1; MS m/z (M+H)⁺ calcd 401.0638, obsd 401.0625.

Synthesis of Phosphate Tris(acetoxymethyl)ester (2)—Silver phosphate (30 mg, 71 µmol) was suspended in 0.5 mL dry CH$_3$CN and AM-Br (22 mg, 145 µmol) was added. After frequent sonication for 20 h at room temperature, another 15 mg (100 µmol) AM-Br was added. When the suspended solid had lost its yellow color, the mixture was centrifuged (1000 rpm, 1 min), and the supernatant was evaporated to dryness and the residue was washed with dry toluene to give phosphate tris(acetoxymethyl)ester (2) as a clear oil (yield 98%); $^1$H NMR (CDCl$_3$, 200 MHz) δ2.15 (s, 9H), 6.45 (d, 6H, J$_{PH}$=13.5 Hz); $^{31}$P NMR (CDCl$_3$, 121.5 MHz) δ−2.25; MS m/z 241 (M-CH$_2$OAc)⁻.

Synthesis of Phenylphosphonate Bis(acetoxymethyl)ester (3)—Phenylphosphonic acid (31.6 mg, 0.2 mmol) and diisopropylethylamine (DIEA, 130 mg, 1.0 mmol) were dissolved in 1 mL dry CH$_3$CN. AM-Br (77 mg, 0.5 mmol) was added and the solution was stirred at room temperature over night. After evaporation of the solvent the solid residue was extracted with dry toluene. Purification of the crude product 3 was performed on a Si60 column (10×40 mm) with 75% toluene/25% ethyl acetate to yield 52 mg 3 (86%) as a clear oil. $^1$H NMR (CDCl$_3$, 200 MHz) δ1.95 (s, 6H), 5.66 (dAB, 4H, J$_{AB}$=5.3 Hz, J$_{PH}$=13.8 Hz, —CH$_2$—), 7.30–7.55 (m, 3H), 7.70 (m, 2H). $^{31}$P NMR (toluene-d$_8$, 121.5 MHz) δ18.70.

Synthesis of N$^6$,O$^{2'}$-Dibutyryl Adenosine 3',5'-cyclic Monophosphate Acetoxymethyl Ester -bt$_2$cAMP/AM (4a/4b)—Two different methods were used to synthesize bt$_2$cAMP/AM. Method A: The sodium salt of N$^6$,O$^{2'}$-dibutyryl cAMP (12.5 mg, 25 µmol) was dissolved in 1 mL MeOH-H$_2$O (1:1) and passed through a Dowex 50W-X8 column (10×40 mm, H⁺-form). The free acid was eluted with 15 mL 50% MeOH. After evaporating to dryness, DIEA (6 mg, 50 µmol) and 1 mL dry CH$_3$CN were added. The reaction was started by the addition of AM-Br (16 mg, 94

μmol). After stirring the solution at room temperature for 4 d, the reaction mixture was chromatographed directly on a Si60 column (10×40 mm, 230–400 mesh) with 95% $CH_3CN$/5% hexane as the eluent under slight pressure. The eluant was collected in 5 mL fractions. Fractions 5–7 contained 5.3 mg (38% yield) of the faster eluating diastereomer of dibutyryl cAMP acetoxymethyl ester (4a) in high purity. $^1H$ NMR ($CDCl_3$, 300 MHz) δ1.05 (t, 3H, J=7.0 Hz), 1.12 (t, 3H, J=7.0 Hz), 1.74 (m, 2H), 1.84 (m, 2H), 2.20 (s, 3H), 2.51 (m, 2H), 2.95 (t, 2H, J=7.0 Hz), 4.36 (ddd, 1H, J=2.7, 10.1, 10.1 Hz, H4'), 4.49 (dd, 1H, J=10.0, 10.0 Hz, $H5'_{ax}$), 4.66 (dddd, 1H, J=2.7, 10.0, 10.0, 22.1 Hz, $H5'_{eq}$), 5.67–5.95 (m, 4H, —$CH_2$—, H2', H3'), 6.04 (s, 1H, H1'), 8.01 (s, 1H, H2), 8.49 (broad s, 1H, $N^6H$), 8.78 (s, 1H, H8); $^{31}P$ NMR ($CDCl_3$, 121.5 MHz) δ –5.0 ppm.

Fractions 8+9 yielded 8.7 mg of a clear oil which contained diisopropylethylammonium bromide and the slower eluting diastereomer of 4b (2:1 w/w as determined by NMR, yield 2.9 mg 4b, 21% from dibutyryl-cAMP). $^1H$ NMR ($CDCl_3$, 200 MHz), δ0.99 (t, 3H, J=7.0 Hz), 1.05 (t, 3H, J=7.5 Hz), 1.70 (m, 4H), 2.18 (s, 3H), 2.45 (t, 2H, J=7.0 Hz), 2.89 (t, 2H, J=7.5 Hz), 4.40–4.70 (m, 3H, H4',$H5'_{eq}$,$H5'_{ax}$), 5.62–5.78 (AB-part of ABX, 2H, $J_{AB}$=5.1 Hz, —$CH_2$—), 5.83 (m, 2H, H2', H3'), 6.01 (s, 1H), 8.02 (broad s, 1H, H2), 8.51 (broad s, 1H, $N^6H$), 8.69 (s, 1H, H8); $^{31}P$ NMR ($CDCl_3$, 121.5 MHz) δ –8.0 ppm; MS (4a/4b 1:1 mixture) m/z $(M+H)^+$ calcd 542.1652, obsd 542.1681.

Method B: 58 mg (0.12 mmol) of the sodium salt of $Bt_2cAMP$ was dissolved in 0.5 mL $H_2O$ and 300 μL 1.8M $AgNO_3$ solution was added. The resulting white precipitate was filtered off washed with $H_2O$, and dried to yield 30.5 mg (45%, 54 μmol) of the silver salt of $Bt_2cAMP$. The white powder was suspended in 1 mL of dry $CH_3CN$ and 51 mg (330 μmol) AM-Br were added. The suspension was frequently sonicated for 4 h at room temperature. The two resulting diastereomeric acetoxymethyl esters 4a and 4b were purified as described under method A to yield 2.8 mg of the fast eluting isomer 4a (10% yield) and 9.6 mg (35%) of the slow eluting diastereomer 4b. NMR and MS analysis of the products of both methods were identical.

Synthesis of $N^2,O^2$'-Dibutyryl Guanosine 3',5'-cyclic Monophosphate Acetoxymethyl Ester bt₂GMP/AM (5a/5b) —The sodium salt of $Bt_2cGMP$ (24 mg, 47 μmol) was passed through Dowex 50W-X8 ($H^+$ form) and the free acid was eluted with 15 mL 50% MeOH. After evaporating to dryness, 1 mL dry acetonitrile, 13 mg (100 μmol) DIEA and 21 mg (135 μmol) AM-Br were added. The solution was stirred overnight, evaporated to dryness, dissolved in $CH_3CN$/hexane (95:5, v/v) and eluted over a Si60 column (10×40 mm) to yield 11 mg (40%) of the two diastereomers of dibutyryl cGMP-AM (5a/5b) as a mixture. $^1H$-NMR (5a only, $CDCl_3$, 200 MHz)δ1.00 (m, 6H), 1.74 (m, 4H), 2.38 (s, 3H), 2.42 (m, 2H), 2.48 (m, 2H), 4.18 (ddd, 1H, J=4.0, 10.0, 10.0 Hz, H4'), 4.30–4.54 (m, 2H, $H5'_{ax}$,$H5'_{eq}$), 5.13 (ddd, 1H, J=1.8, 4.1, 10.0 Hz, H3'), 5.56 (dd, 1H, J=4.1, 4.1 Hz, H2'), 5.71 (dAB, 2H, J=12.5, 9.1 Hz, —$CH_2$—), 6.04 (d, 1H, J=4.0 Hz, H2'), 7.65 (broad s, 1H, $N^2H$), 10.14 (s, 1H, H8), 12.30 (broad s, 1H, $N^1H$); $^{31}P$ NMR ($CDCl_3$, 121.5 MHz) δ –5.5 and –8.5 ppm; MS m/z $(M+H)^+$ calcd 558.1601, obsd 558.1611.

The most general and economical synthetic route to acetoxymethyl phosphate esters is believed to be alkylation of the parent phosphate anions by acetoxymethyl halides. The instability of acetoxymethanol precludes its phosphorylation. Preliminary synthetic attempts, similar to the experiments of Srivasta and Farquhar (15), were performed on 4-methylumbelliferyl phosphate and phenyl phosphonate as readily available model compounds detectable by UV absorption and bearing no competing nucleophilic centers. 4-Methylumbelliferyl phosphate bis(acetoxymethyl)ester (Table I—1) was successfully prepared in 73% yield by suspending the disilver salt of 4-methylumbelliferyl phosphate in dry acetonitrile, adding acetoxymethyl bromide (AM-Br) (38), and sonicating the heterogeneous mixture at frequent intervals for 24h. The $^1H$ NMR of the supernatant showed an AB doublet at 5.7 ppm for the methylene group of the acetoxymethyl ester, a typical pattern for all phosphate acetoxymethyl esters reported here. The synthesis of phosphate tris(acetoxymethyl)ester (Table I—2) offered a possibility to directly monitor the progress of the reaction. Yellow $Ag_3PO_4$ was reacted with AM-Br as described above. Disappearance of the color after 36 h indicated completion of the reaction. The product was the only compound in the organic phase (98% yield).

An alternative to silver salts is desirable for polyphosphates or molecules bearing oxidizable functionalities. Direct treatment of phenylphosphonic acid with an excess of the hindered base diisopropylethylamine (DIEA) and AM-Br eventually gave an 86% yield of the phenylphosphonate bis(acetoxymethyl)ester (Table I—3).

Analogous reactions worked, albeit in lower yield, for $N^6,2$'-O-dibutyryl adenosine 3',5'-cyclic monophosphate acetoxymethyl ester ($Bt_2cAMP$/AM, 4a/4b) and $N^2,2$'-O-dibutyryl guanosine 3',5'-cyclic monophosphate acetoxymethyl ester ($Bt_2cGMP$/AM, 5a/5b). The commercially available sodium salts of $Bt_2cAMP$ and $Bt_2cGMP$ were converted into the free acids on Dowex 50W-X8 and then into DIEA salts. Reaction took place in dry $CH_3CN$ with an excess of DIEA and AM-Br for 5 days at room temperature. Both nucleotide AM-esters were purified on silica gel 60 ($CH_3CN$/hexane 19:1 v/v) after evaporation of the solvent. The two diastereomers of $Bt_2cAMP$/AM (4a/4b) were isolated in yields of 37% and 21% for the fast and slow-eluting isomers, the latter co-eluting with residual DIEA. $^{31}P$-NMR resonances were –5.0 ppm and –8.0 ppm, respectively, but absolute configurations were not determined. The analogous two diastereomers of $Bt_2cGMP$/AM (5a/5b) could not be separated under the described conditions, but were free of DIEA. $Bt_2cAMP$/AM was also prepared by alkylating the silver salt of $Bt_2cAMP$ with AM-Br in $CH_3CN$ with frequent sonication for 24 h. These heterogeneous conditions reversed the enantiomeric preference, giving the fast and slow-migrating isomers in 10% and 35% yields.

The following biological tests were conducted to demonstrate the biological activity of the cAMP derivative after it passes into the cell.

Activation of intracellular protein kinase A. The premier target of cAMP in most cells is the cAMP-dependent protein kinase (PKA) (45). To show that this enzyme can be activated by extracellular application of $Bt_2cAMP$/AM, we used a recently-developed assay for PKA activation in single cells (39). When PKA is doubly labeled with fluorescein on its catalytic subunits and rhodamine on its regulatory subunits to produce FlCRhR, fluorescence energy transfer from the fluorescein to rhodamine occurs in the holoenzyme complex but is disrupted upon activation and dissociation of the subunits. The change in the ratio of fluorescein to rhodamine emissions parallels the increase in kinase activity and can be nondestructively imaged in single cells. REF-52 fibroblasts were microinjected with FlCRhR and emission ratio images recorded at room temperature as previously described (27). 30 min after injection, 0.1, 1, or 10 μM $Bt_2cAMP$/AM were added extracellularly (FIG. 1—Graph A). The highest dose yielded a maximal change in fluorescence ratio within 15 min. The intermediate dose gave a shallower slope and a lower plateau to slightly over 50% of the maximal change. The onset of the separation of regulatory and catalytic subunit of FlCRhR occurred roughly 2 min after the addition of the cAMP derivative. Much the same delay and overall time course occurred with non-esterified Bt$_2$cAMP, though much higher concentrations, 1 mM, were required (FIG. 1—Graph B). Other widely used, supposedly lipophilic cAMP derivatives showed no delay in beginning to activate PKA, but millimolar concentrations were still required (FIG. 1—Graphs C & D).

To show that intracellular enzymatic hydrolysis of the ester groups is required we examined the binding properties of Bt$_2$cAMP/AM and Bt$_2$cAMP to FlCRhR in vitro. The highest concentration of Bt$_2$cAMP/AM used in the other assays (10 μM) gave no separation of the subunits, while Bt$_2$cAMP was roughly 1/100 as potent as cAMP probably due to contamination by 1% monobutyryl-cAMP as specified by the supplier (Sigma) (See Table II).

TABLE II

In-vitro cAMP-dependent kinase activation assay.

|  | cAMP |  | Bt$_2$cAMP[a] |  | Bt$_2$cAMP/AM |
|---|---|---|---|---|---|
| concentration [μM] | 1 | 10 | 200[b] | 10 | 100 | 10 |
| % kinase[c] activation | 67 | 91 | 100 | 16 | 61 | 0 |

[a]The slight residual activity of Bt$_2$cAMP is probably due to an impurity of N$^6$-monobutyryl cAMP (1%) as specified by the supplier.
[b]200 μM cAMP was considered the maximal dose necessary to fully dissociate FlCRhR.
[c]Labelled cAMP-dependent kinase type I (FlCRhR). This labelled isoform is more stable against subunit dissociation in the absence of cAMP at the low enzyme concentrations used in this assay than labelled type II.

Figure 2A:
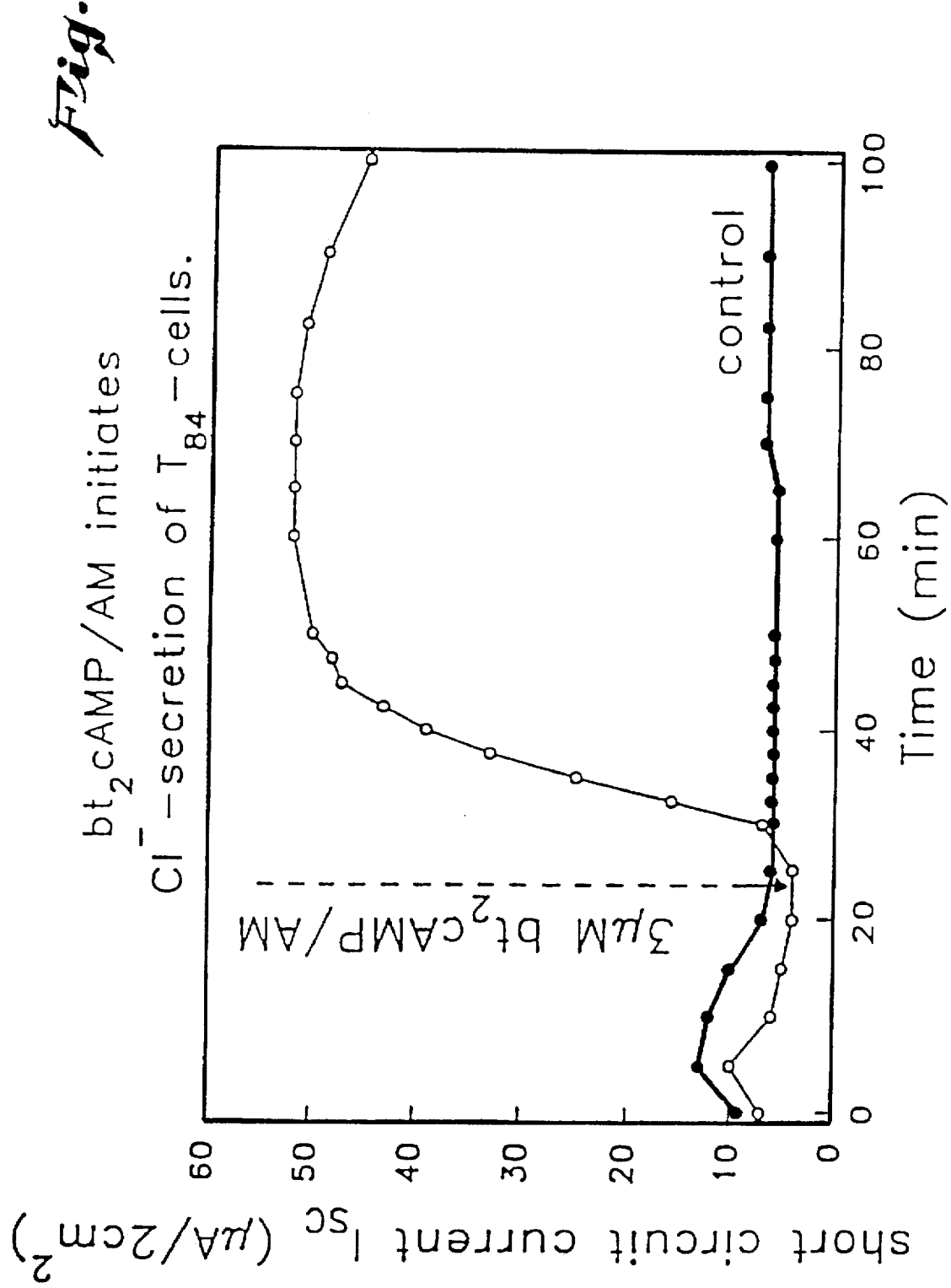
FIG. 2A is a graphic representation of the results of tests showing the initiation of $Cl^-$ secretion by $Bt_2cAMP/AM$.

One of the many well-known cell functions controlled by cAMP is intestinal transepithelial Cl$^-$-secretion (46). A convenient test system is the intestinal cell line T$_{84}$, in which chloride secretion can be continuously monitored by mounting confluent monolayers of cells in Ussing chambers (42). FIG. 2A shows the Cl$^-$-secretion measured as short circuit current (I$_{SC}$) across the cells. The addition of Bt$_2$cAMP/AM at a concentration of 3 μM to the serosal bathing solution caused an increase in I$_{SC}$ with a maximum after 20 min. Higher concentrations of the derivative caused faster but not significantly greater responses, whereas lower concentrations reached lower maximum I$_{SC}$ values. The I$_{SC}$ values obtained at an arbitrary intermediate time, 12 min after addition of various cAMP-derivatives, were used to determine the dose dependency (FIG. 2B). The dose response curves were parallel, with EC$_{50}$ values of 2 μM and 400 μM for Bt$_2$cAMP/AM and Bt$_2$cAMP respectively. Therefore the introduction of the acetoxymethyl group on the phosphate increased the potency by 200 fold in this assay by circumventing the permeability barrier. Furthermore, the acetoxymethyl ester seems to be cleaved inside T$_{84}$ cells without significant delay, since the two agents gave essentially indistinguishable kinetics of activation. Tests with the cAMP-derivatives 8-Br-cAMP and 8-pCPT-cAMP showed activation of Cl$^-$-secretion with EC$_{50}$ values of 1.5 mM and 100 μM, respectively.

Figure 3B:
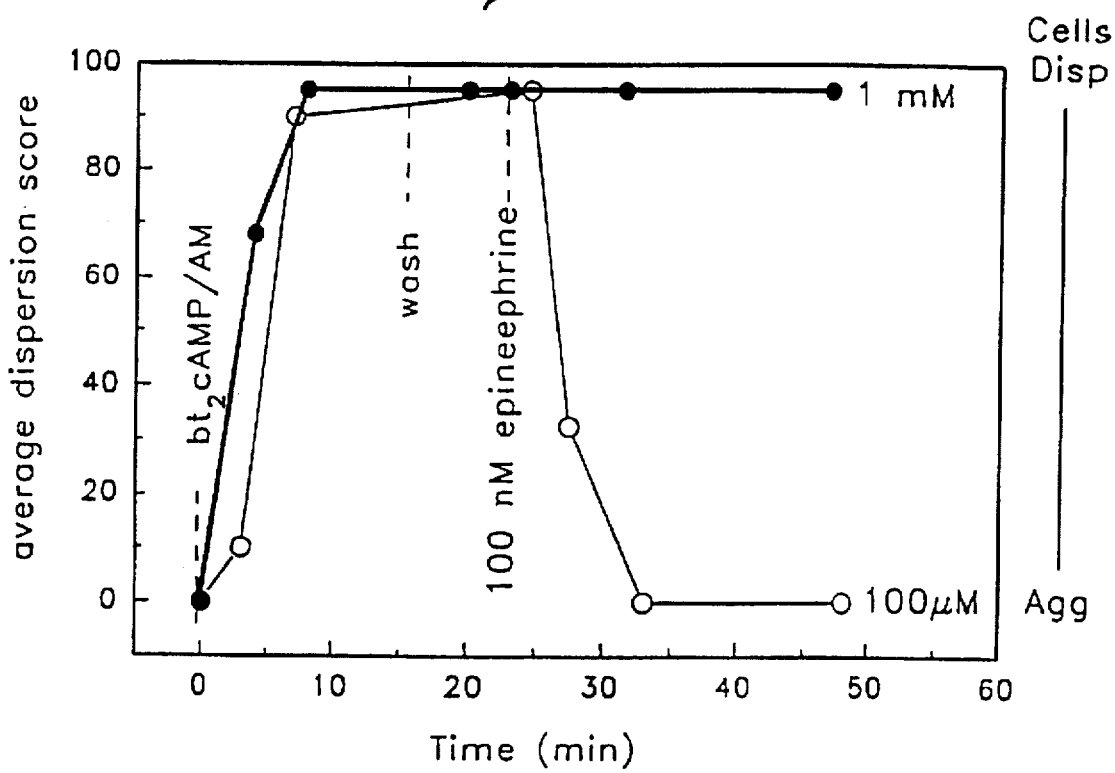
FIG. 3B is a graph showing test results demonstrating the reversibility of the dispersion shown in FIG. 3A.

Fish dermal chromatophores exhibit a tightly regulated movement of pigment granules either inward into a highly aggregated central mass, or outward, dispersing the pigment throughout the cell. In angelfish (*Pterophyllum scalare*) melanophores this movement is microtubule based and cAMP regulated (44,47) but relatively refractory to external cAMP analogs. Melanophores permit a visual single-cell assay for the ability of cAMP analogs to enter cells and mimic cAMP actions. The melanophores were isolated on angelfish scales and the epidermis was stripped off. The 60–100 melanophores per scale were pretreated with an α$_2$-adrenergic agonist to reduce endogenous cAMP and start with full aggregation. Extracellular Bt$_2$cAMP/AM then caused dispersion of the pigment in a dose-dependent manner (FIG. 3A). A concentration of 100 μM Bt$_2$cAMP/AM was enough to cause essentially complete dispersal; however, 1 mM gave a slightly faster onset of action and could not be readily reversed by removal of the extracellular Bt$_2$cAMP/AM and administration of epinephrine, whereas the effect of 100 μM was easily reversed (FIG. 3B). Dispersion was just detectable at 1 μM and half-maximal near 10 μM (FIG. 3A). By comparison, 1 mM Bt$_2$cAMP was unable to cause any detectable dispersion. Hence the AM ester group increased the potency by more than 1000 in this assay. The effectiveness of Bt$_2$cAMP/AM shows that the inertness of Bt$_2$cAMP in melanophores is due to poor permeability rather than susceptibility of Bt-cAMP to phosphodiesterases or selectivity of kinase binding sites for cAMP substitution (48). The preceding examples are summarized in (64).

Examples of synthesis and use of preferred exemplary inositol polyphosphate acetoxymethyl esters in accordance with the present invention is as follows:

Proton and $^{31}$P NMR spectra were obtained in CDCl$_3$, DMSO-d$_6$, toluene-d$_8$, or CD$_3$OD with residual CHCl$_3$ (δ=7.26 ppm), DMSO-d$_5$ (δ=2.49 ppm), toluene-d$_7$ (δ=7.30 ppm), or CHD$_2$OD (δ=3.32 ppm) being used as the internal standards for $^1$H spectra, respectively. 85% phosphoric acid was used as an external standard for $^{31}$P spectra. All NMR spectra were recorded on either a Varian Gemini-200 (200 MHz), a Bruker WH-360 (360 MHz) or a General Electric QE-300 (300 MHz) spectrometer. Fast atom bombardment mass spectroscopy (FAB-MS) and precise mass determinations were performed by the mass spectroscopy facilities of the University of Bremen, FRG, or University of California, Riverside. Matrices were glycerol, tetraethylene glycol or polyethylene glycol. Elemental microanalyses were performed by Beller, FRG. Melting points were measured on an electrothermal melting point apparatus and are uncorrected. HPLC separations were performed on 10 μm RP-18 LiChrosorb (Merck, FRG, 4×250 mm, analytical separations) and 10 μm RP-8 RSiL (Biorad, 22×250, preparative separations). Preparative flash chromatography was performed on silica gel Si60 (230–400 mesh, Merck, FRG) or RP-8 LiChroprep (25–40 μm, Merck, FRG).

Pyridine and acetonitrile were stored over activated molecular sieve (3 Å) for at least 3 d. All other solvents were purchased in highest purity available and were used as received. N,N-Diisopropylethylamine (DIEA) was distilled from CaH$_2$. Acetoxymethyl bromide (AM-Br) (46), dibenzyl N,N-diethyl phosphoramidite (49), and 1,4,5,6-tetra-O-benzyl myo-inositol (50,51) were prepared according to known procedures. Fura-2/AM and 2',7'-bis(2-carboxyethyl) -5- (and -6) -carboxyfluoroscein/acetoxymethyl (BCECF/AM) were from Molecular Probes. Vasopressin, ionomycin, and nigericin were from Calbiochem. Thapsigargin was from LC Services Corp. All other reagents were from Aldrich.

Figure 4A:
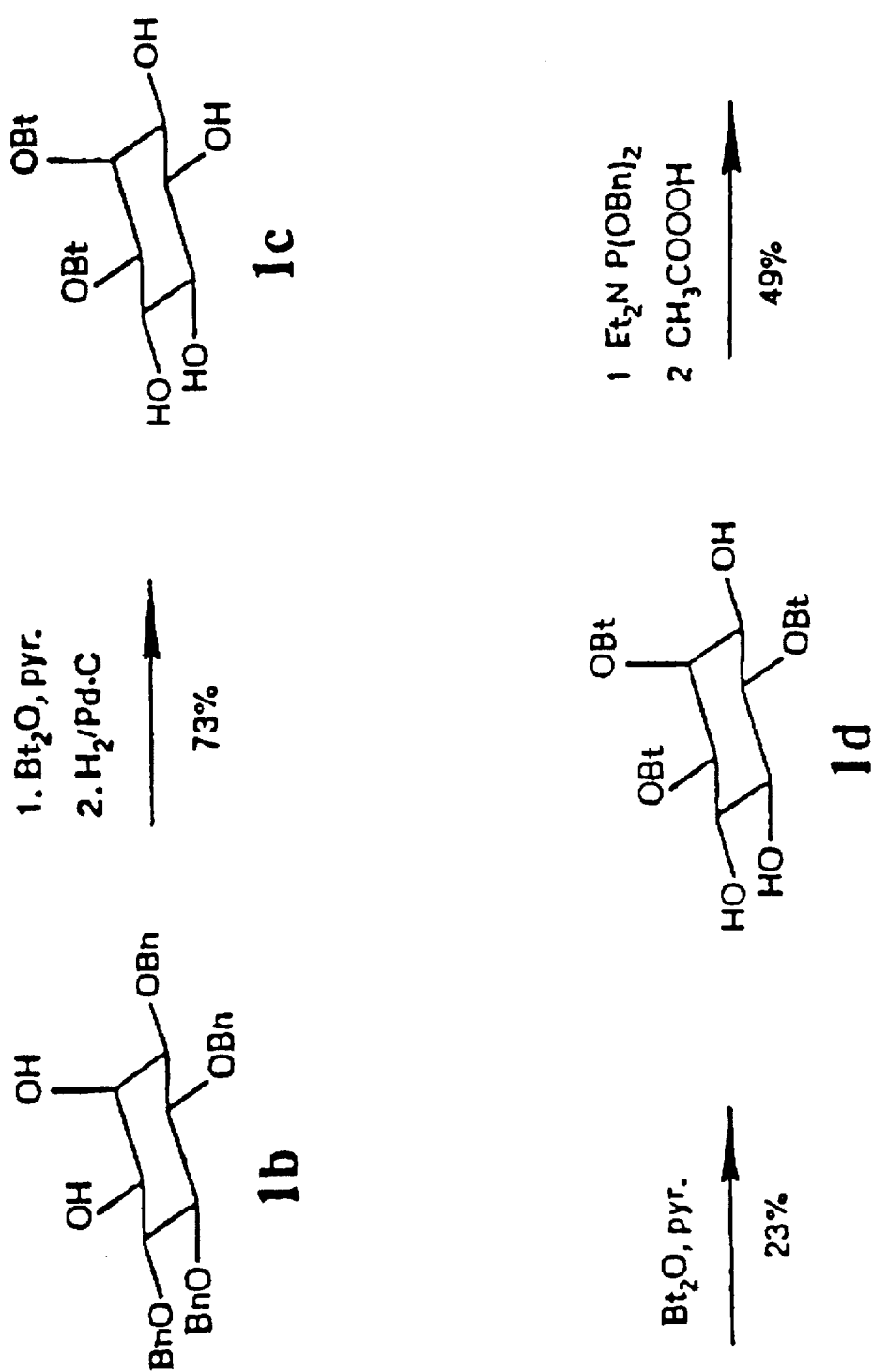
FIG. 4 is a schematic representation of the synthesis of $Bt_3IP_3/AM$.
Figure 4B:
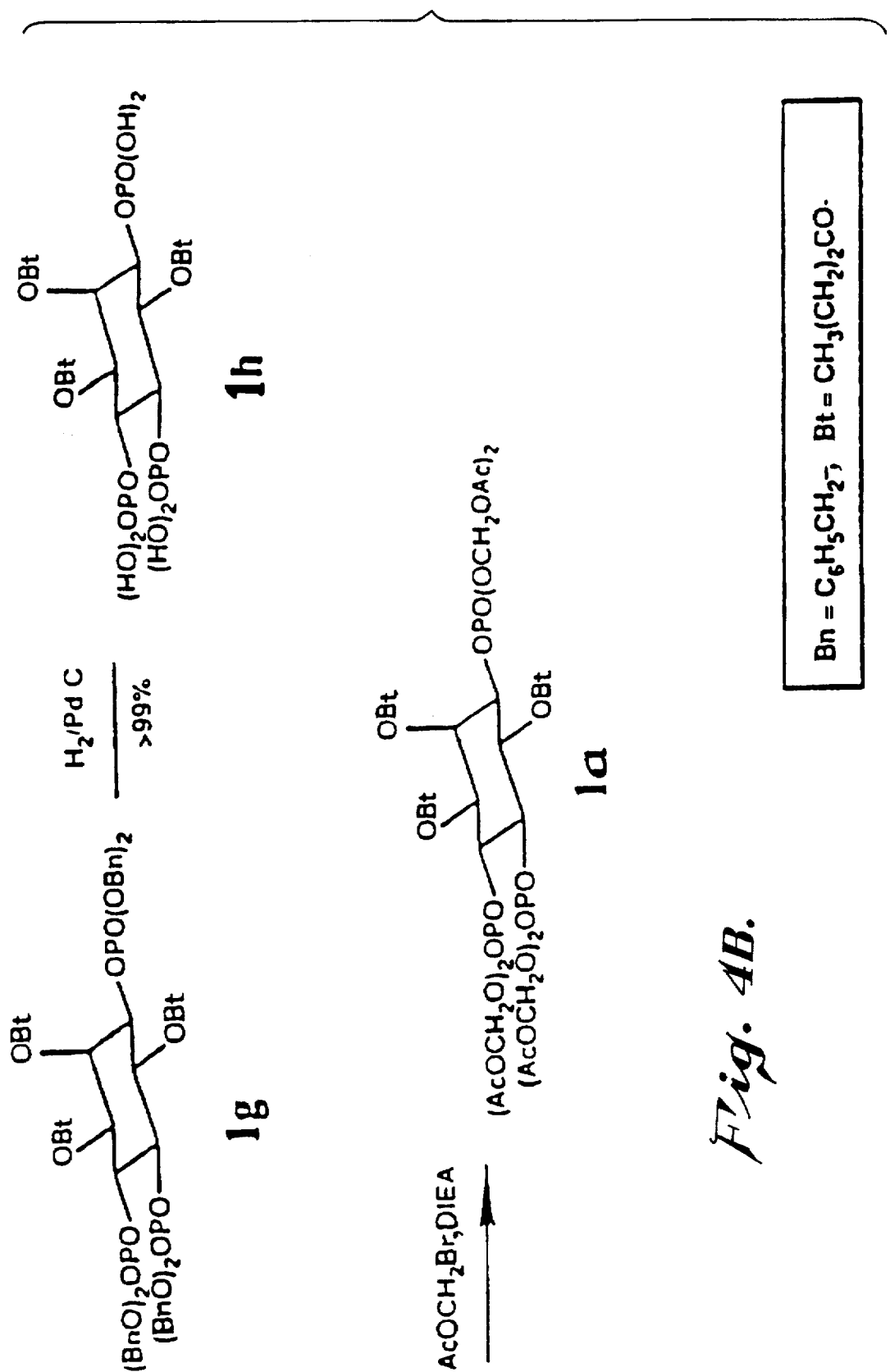

The synthesis of 2,3,6-Tri-O-Butyryl-myo-Inositol 1,4,5-Triphosphate Hexabis (acetoxymethyl)ester (1a) is shown in FIG. 4. The synthesis is as follows:

Synthesis of 2,3-Di-O-Butyryl myo-Inositol (FIG. 4—1c). A solution of 1,4,5,6-tetra-O-benzyl myo-inositol (FIG. 4—1b) (10 g, 18.6 mmol) and n-butyric anhydride (15.4 mL, 100 mmol) in 50 mL of dry pyridine was stirred at room temperature for 4 days. After evaporation at reduced pressure the resulting oil was dissolved in 100 mL glacial acetic acid and 1.06 g (1 mmol) Pd/C (10%) was added. $H_2O$ was bubbled through the reaction mixture for 4 h at room temperature. The catalyst was removed by ultrafiltration and crude 2,3-di-O-butyryl myo-inositol (FIG. 4—1c) was obtained by direct lyophilization. Recrystallization from acetone yielded 4.34 g (73%); m.p. 141°–142° C.; $^1H$ NMR ($CD_3CN/D_2O$, 360 MHz)$\delta$1.01 (t, 3H, J=7.5 Hz), 1.06 (t, 3H, J=7.5 Hz), 1.69 (m, 2H), 1.74 (m, 2H), 2.34 (m, 2H), 2.45 (t, 2H, J=7.5 Hz), 3.50 (dd, 1H, J=9.2, 9.2 Hz, H5), 3.74 (dd, 1H, J=9.5, 9.5 Hz, H4), 3.80 (dd, 1H, J=3.0, 9.6 Hz, H3), 3.84 (dd, 1H, J=9.2, 10.0 Hz, H6), 4.92 (dd, 1H, J=3.0, 10.1 Hz, H1), 5.57 (dd, 1H, J=3.0, 3.0 Hz, H2); MS m/z (M-H)$^-$ 319. Anal. Calcd for $C_{14}H_{24}O_8$: C, 52.48; H, 7.57. Found: C, 52.36; H, 7.46.

Synthesis of 2,3,6- (FIG. 4—1d), 2,3,5-(1e) and 1,2,3-Tri-O-Butyryl myo-Inositol (1f). A solution of the dibutyrate FIG. 4—1c (2.0 g, 6.25 mmol) in pyridine was stirred with 0.98 mL (6.0 mmol) n-butyric acid anhydride for 24 h at room temperature. After evaporation under reduced pressure, the oily residue was dissolved in MeOH and purified by flash chromatography (RP-8, 45% MeOH) to yield 0.53 g (23%) 1d, 0.12 g (5%) 1e and 1.16 g (50%) 1f. 1d: $^1H$ NMR ($CDCl_3$, 360 MHz)$\delta$0.85–1.05 (m, 9H), 1.65 (m, 6H), 2.30–2.43 (m, 7H), 2.47 (d, 1H, J=3.3, —OH), 2.61 (d, 1H, J=4 Hz, —OH), 3.58 (ddd, 1H, J=3.5, 9.5, 9.9 Hz, H5), 3.84 (ddd, 1H, J=2.7, 7.0, 10.0 Hz, H3), 3.92 (ddd, 1H, J=4.0, 10.0, 10.0 Hz, H6), 4.84 (dd, 1H, J=3.0, 10.1, H1), 5.14 (dd, 1H, J=10.0, 10.0 Hz, H4), 5.57 (dd, 1H, J=3.0, 3.0 Hz, H2); MS m/z (M-H)$^-$ 389. Anal. Calc. for $C_{18}H_{30}O_9$: C, 55.36; H, 7.76. Found: C, 55.28; H, 7.64. 1e: $^1H$ NMR ($CDCl_3$, 360 MHz) $\delta$(m, 9H), 1.67 (m, 6H), 2.29 (t, 2H, J=7.5 Hz), 2.39 (m, 4H), 3.81 (m, 2H, H3,H4), 3.92 (dd, 1H, J=10.5, 10.5 Hz, H6), 4.94 (dd, 1H, J=9.6, 9.6 Hz, H5), 4.94 (dd, 1H, J=2.6, 10.0 Hz, H1), 5.55 (dd, 1H, J=2.6, 2.6 Hz, H2). MS m/z (M-H)$^-$ 389. 1f: $^1H$ NMR ($CDCl_3$, 360 MHz)$\delta$0.90–1.03 (m, 9H), 1.63 (m, 6H), 2.28 (m, 2H), 2.35 (t, 4H, J=7.2 Hz), 3.59 (dd, 1H, J=9.9, 9.9 Hz, H5), 3.88 (m, 2H, H4,H6), 4.98 (m, 2H, H1,H3), 5.53 (dd, 1H, J=3.2, 3.2 Hz, H2). MS m/z (M-H)$^-$ 389.

Synthesis of 2,3,6-Tri-O-Butyryl myo-Inositol 1,4,5-Tris (dibenzyl)phosphate (FIG. 4—1g). 2,3,6-Tri-O-butyryl myo-inositol (FIB. 4—1d) (70 mg, 180 µmol) was dissolved in 6 mL dry $CH_3CN$ and added to 1.5 mmol freshly prepared dibenzyl N,N-diethyl phosphoramidite. 1H-tetrazole (105 mg, 1.5 mmol) was added and the mixture was stirred overnight. Oxidation took place at –40° C. by slowly adding 340 µL $CH_3COOOH$ (30% w/w in AcOH, 1.5 mmol). The solution was allowed to warm up to room temperature. The solvent was removed, and the resulting oil as redissolved in 20 mL ether and subsequently washed with 5% $NaHSO_3$ (pH 4), 10% $NaHCO_3$ and $H_2O$ (2×20 mL each). After drying with $Na_2SO_4$, the organic layer was evaporated to give a clear oil. Chromatography by preparative HPLC (RP-8, 91% MeOH) yielded 100 mg (48%) of the desired fully protected inositol trisphosphate FIG. 4—1 g as a white powder; m.p. 75° C. $^1H$ NMR ($CDCl_3$, 360 MHz) $\delta$0.66, 0.78, 0.95 (3t, 3H each, all J=7.4 Hz), 1.24–1.70 (m, 6H), 2.02 (t, 2H, J=7.5 Hz), 2.10 (m, 2H), 2.36 (t, 2H, J=7.5 Hz), 4.45 (ddd, 1H, J=3.5, 8.5, 9.5 Hz, H3), 4.49 (ddd, 1H, J=9.0, 9.0, 10.0 Hz, H5), 4.80–5.10 (m, 14H, —$CH_2$—,H3,H4), 5.59 (dd, 1H, J=9.5, 10.0 Hz, H6), 5.71 (dd, 1H, J=3.2, 3.2 Hz, H2), 7.28 (m, 30H). $^{31}P$ NMR ($CDCl_3$, 145.8 MHz) $\delta$–0.9, –1.3, –1.5. MS m/z (M-$C_7H_7$)$^-$ 1079.

Synthesis of 2,3,6-Tri-O-Butyryl myo-Inositol 1,4,5-Trisphosphate (FIG. 4—1h). A mixture of FIG. 4—1g (76 mg, 65 µmol) and Pd/C (10%) (106 mg, 100 µmol) in glacial acetic acid was hydrogenated at room temperature and atmospheric pressure for 3 h. After filtration (Whatman GF/A) and lyophilization the product was obtained as a white powder in 99% yield (free acid, 40.6 mg). $^1H$ NMR ($D_2O$, 200 MHz) $\delta$0.89 (m, 9H), 1.60 (m, 6H), 2.32 (m, 2H), 2.42 (m, 4H), 4.38 (ddd, 1H, J=10.0, 10.0, 10.0 Hz, H5), 4.42 (ddd, 1H, J=3.0, 9.5, 10.0 Hz, H1), 4.61 (ddd, 1H, J=9.7, 10.0, 10.0 Hz, H4), 5.14 (dd, 1H, J=3.0, 10.0 Hz, H3), 5.36 (dd, 1H, J=10.0, 10.0 Hz, H6), 5.68 (dd, 1H, J=3.0, 3.0 Hz, H2). $^{31}P$ NMR (DMSO-$d_6$, 145.8 MHz) $\delta$–0.7, 0.0, 0.4. MS m/z (M-H)$^-$ calcd 629.0802, obsd 629.0826.

Synthesis of 2,3,6-Tri-O-Butyryl myo-Inositol 1,4,5-Trisphosphate Hexakis(acetoxymethyl)ester ($Bt_3IP_3$/AM, FIG. 4—1a). A solution of the free acid 1h (9.5 mg, 15 µmol) in 1 mL of dry $CH_3CN$ was evaporated to dryness, DIEA (22 mg, 170 µmol) and 1 mL dry $CH_3CN$ was added, and the suspension was dried again in high vacuum. Subsequently, dry $CH_3CN$ (0.5 mL), DIEA (44 mg, 340 µM), and acetoxymethyl bromide (150 mg, 950 µM) were added. The mixture was stirred under argon for 2 days at room temperature, the solvent was evaporated in high vacuum, and the hexakis acetoxymethyl ester 1a was extracted from the solid residue with toluene to yield 33%. $^1H$ NMR (toluene-$d_8$, 200 MHz) $\delta$0.70 (t, 3H, J=7.0 Hz), 0.85 (t, 3H, J=7.5 Hz), 0.99 (t, 3H, J=7.5 Hz), 1.50 (m, 4H), 1.65–1.90 (m, 2H), 1.74 (s, 3H), 1.75 (s, 3H), 1.78 (2s, 6H), 1.79 (s, 3H), 2.20–2.70 (m, 6H), 4.85 (ddd, 1H, J=7.2, 7.2, 8.0, H5), 4.90 (m, 1H, H1), 5.25–5.85 (m, 15H, —$CH_2$—, H3, H4, H6), 6.00 (dd, 1H, J=3.2, 3.2 Hz, H2); $^{31}P$ NMR (toluene-$d_8$, 121.5 MHz) $\delta$–4.00, –4.10, –4.25 (1:1:1); MS m/z 989 (M-$CH_2OAc$)$^-$.

Figure 5A:
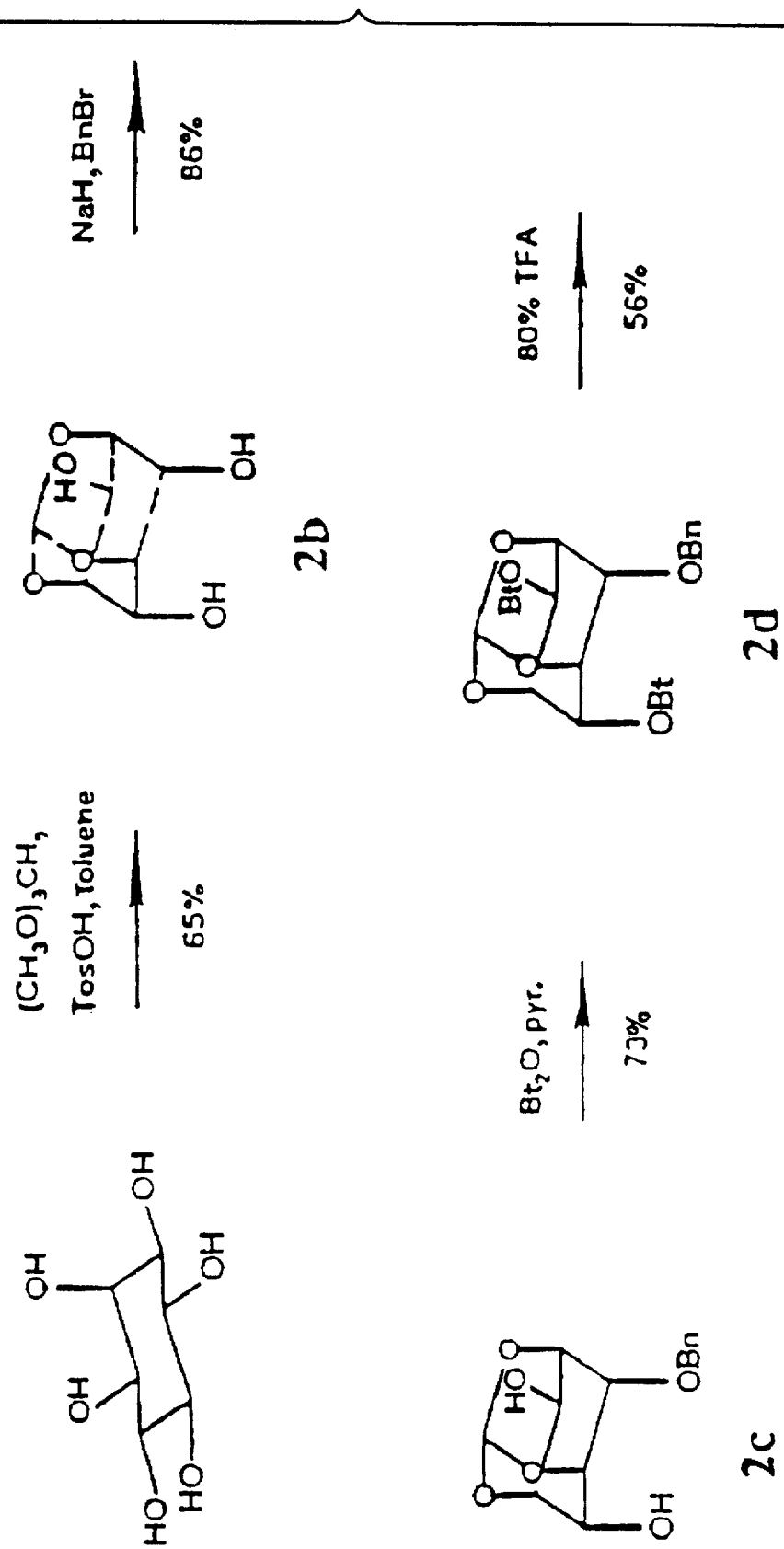
FIG. 5 is a schematic representation of the synthesis of $Bt_2IP_4/AM$.
Figure 5B:
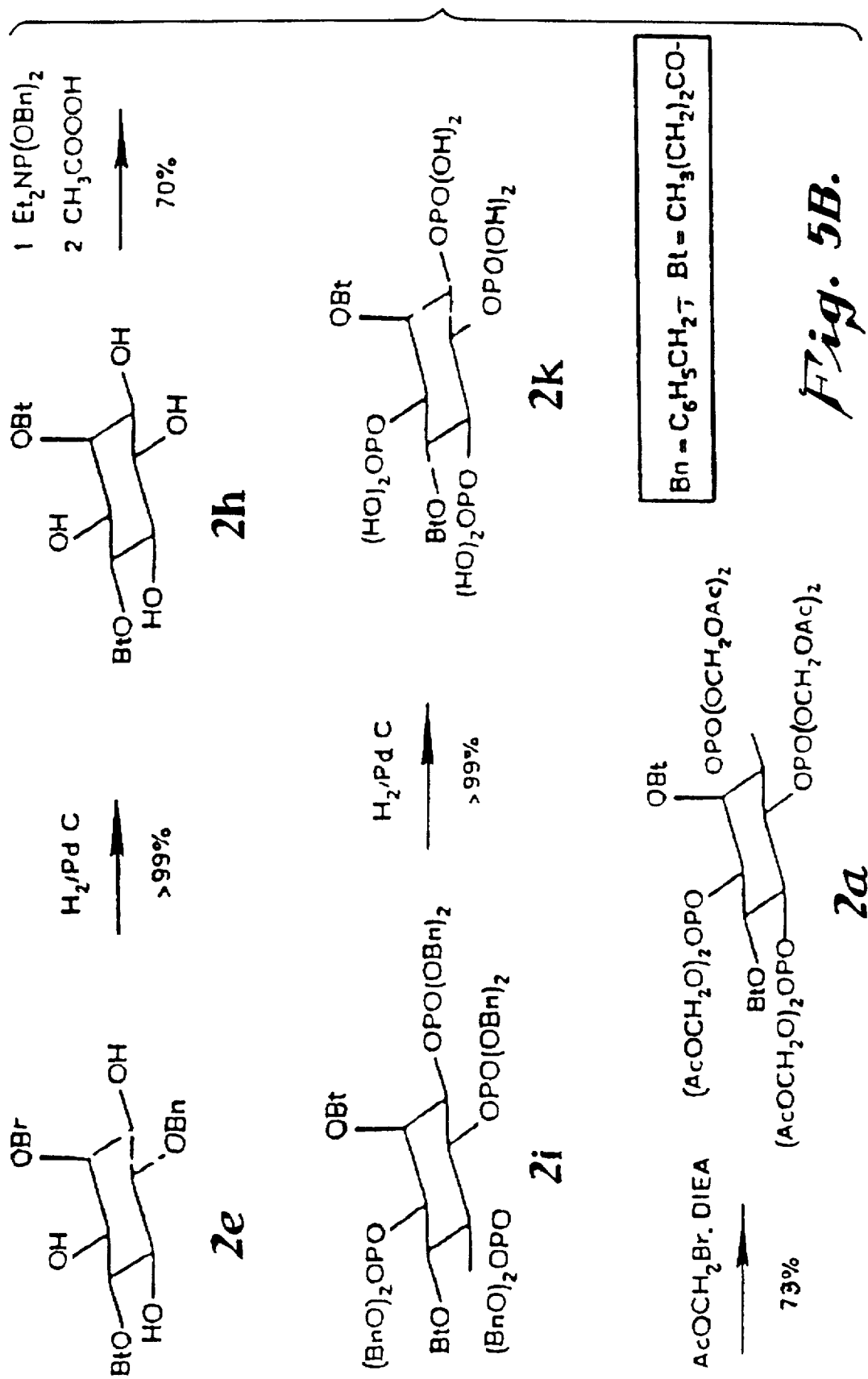

Synthesis of 2,6-Di-O-Butyryl myo-Inositol 1,3,4,5-Tetrakisphosphate Octakis (acetoxymethyl) ester ($Bt_2IP_4$/AM) is shown in FIG. 5. The synthesis is as follows:

Synthesis of myo-Inositol 1,3,5-Orthoformate (FIG. 5—2b). 2b was prepared from myo-inositol (9 g, 50 mmol) according to the procedure of Lee and Kishi (52) except that trimethyl orthoformate was used instead of triethyl formate. The crude product initially isolated from a silica column as a black oil was filtered through activated charcoal to yield the pure product (6.2 g, 65% yield). Recrystallization from MeOH gave rhombic crystals, m.p. 300°–302° C. (sealed tube).

Synthesis of 4-O-Benzyl-myo-Inositol 1,3,5-Orthoformate (FIG. 5—2c). 2c was prepared from the orthoester 2b (0.5 g, 2.63 mmol) by benzylation of the monoanion according to known procedures (53). Analysis data are consistent with those of Baudin et al (54).

Synthesis of 4-O-Benzyl 2,6-di-O-Butyryl myo-Inositol 1,3,5-Orthoformate (2d). The monobenzyl ether 2c (400 mg, 1.79 mmol) was butyrylated under standard conditions (n-butyric anhydride/pyridine at room temperature) to yield 438 mg (73% yield, colorless crystals) of the dibutyrate 2d after recrystallization from MeOH. m.p.: 97° C.; $^1H$ NMR ($CDCl_3$, 200 MHz) $\delta$0.83 (t, 3H, J=7.5 Hz), 1.00 (t, 3H, J=7.5 Hz), 1.50 (m, 2H), 1.72 (m, 2H), 2.12 (m, 2H), 2.47 (t, 2H, J=7.5 Hz), 4.30 (m, 1H, H1), 4.38 (m, 2H, H3,4), 4.59 (AB, 2H, J=11 Hz, —$CH_2$—), 4.64 (m, 1H, H5), 5.33 (ddd, 1H, J=1.1, 2.0, 2.0 Hz, H2), 5.42 (ddd, 1H, J=1.8, 4.0, 5.0 Hz, H6), 5.56 (d, 1H, J=1.1 Hz, H7), 7.43 (m, 5H). MS m/z (M-H)$^-$ calcd 419.1706, obsd 419.1689.

Synthesis of 4-O-Benzyl 2,6-di-O-Butyryl myo-Inositol (FIG. 5—2e). The fully protected inositol derivative 2d was dissolved in 10 mL CF₃COOH (80% in water) and stirred for 7 h at room temperature. After evaporation to dryness, the crude product 2e was purified on preparative HPLC (RP-8) to collect three fractions. The main fraction (80% by HPLC) gave the desired product 2e (210 mg, 56% yield) in high purity; $^1$H NMR (CDCl₃, 200 MHz) δ1.00 (m, 6H), 1.69 (m, 4H), 2.40 (m, 4H), 3.68 (m, 4H, H1,3,4,5), 4.83 (s, 2H, —CH₂—), 5.12 (m, 1H, H6), 5.50 (dd, 1H, J=2.5, 2.5 Hz, H2), 7.34 (s, 5H); MS m/z (M-H)⁻ calcd 409.1862, obsd 409.1881.

An earlier eluting fraction contained a mixture of 4-O-benzyl 6-O-butyryl myo-inositol (2f) and 4-O-benzyl 2-O-butyryl myo-inositol (2g).

Synthesis of 4-O-Benzyl 2-O-Butyryl myo-Inositol (FIG. 5—2g). Recrystallization gave the minor product 2g (8 mg, 2% yield); m.p. 115° C.; $^1$H NMR (CDCl₃, 200 MHz) δ0.86 (t, 3H, J=7.3 Hz), 1.55 (m, 2H), 2.26 (t, 2H, J=7.4 Hz), 2.78 (m, 3H, OH), 3.02 (d, 1H, J=2.4 Hz, C2-OH), 3.40 (m, 3H, H1,3,5), 3.55 (dd, 1H, J=9.5, 9.5 Hz, H4), 3.94 (ddd, 1H, J=2.4, 2.4, 2.4 Hz, H2), 4.75 (AB, 2H, J=11.5 Hz, —CH₂—), 5.01 (dd, 1H, J=10.0, 10.0 Hz, H4), 7.20 (m, 5H); MS m/z (M-H)⁻ calcd 339.1444, obsd 339.1450.

Synthesis of 2,6-Di-O-Butyryl myo-Inositol (FIG. 5—2h). A mixture of 2e (0.46 mmol) and 106 mg Pd/C (10%) (0.1 mmol Pd) in glacial acetic acid was stirred under H2 for 3 h at room temperature. Filtration (Whatman GF/A) and lyophilization yielded 148 mg (>99% yield) of the inositol dibutyrate 2h as a clear oil. $^1$H NMR (CD₃OD, 200 MHz) δ0.99 (m, 6H), 1.70 (m, 4H), 2.41 (m, 4H), 3.35 (m, 1H, H5), 3.55 (m, 1H, H1), 3.62 (dd, 1H, J=10.0, 10.0 Hz, H6), 3.72 (dd, 1H, J=2.5, 10.5 Hz, H3), 5.11 (dd, 1H, J=10.5, 10.5 Hz, H4), 5.47 (dd, 1H, J=2.5, 2.5 Hz, H2); MS m/z (M-H)⁻ calcd 319.1393, obsd 319.1388.

Synthesis of 2,6-Di-O-Butyryl myo-Inositol 1,3,4,5-Tetrakis(dibenzyl)phosphate (FIG. 5—2i). A solution of 2h (136 mg, 0.44 mmol) and tetrazole (350 mg, 5 mmol) was added to freshly prepared dibenzyl N,N-diethyl phosphoramidite (1.59 g, 5 mmol). The mixture was stirred under argon overnight and then cooled down to −40° C. CH₃COOOH (1.12 mL, 5 mmol, 32% w/w in acetic acid) was added and the solution was allowed to warm up to room temperature. The solvents were removed, and the resulting oil was dissolved in 30 ml ether and washed twice with 20 mL of each of the following solutions: 5% NaHSO₃ (pH 4), 10% NaHCO₃, H₂O. After drying with Na₂SO₄ the organic layer was evaporated to yield a clear oil. The crude product 2i was purified by preparative HPLC on RP-8, eluting with 93% MeOH. Yield: 436 mg, 72%. $^1$H NMR (CDCl₃, 200 MHz) δ0.63 (t, 3H, J=7.0 Hz), 0.94 (t, 3H, J=7H), 1.31 (m, 2H), 1.64 (m, 2H), 2.08 (m, 2H), 2.38 (t, 2H, J=7 Hz), 4.27–4.51 (m, 3H, H1,3,5), 4.82–5.14 (m, 17H), 5.56 (dd, 1H, J=10.0, 10.0 Hz), 6.06 (dd, 1H, J=3.0, 3.0 Hz), 7.08–7.40 (m, 40H); $^{31}$P NMR (CDCl₃, 150 MHz) δ−0.62, −0.99, −1.07, −1.36; MS m/z (M-C₇H₇)⁻ 1271 and (M-H)⁻ 1361.

Synthesis of 2,6-Di-O-Butyryl myo-Inositol 1,3,4,5-Tetrakisphosphate (FIG. 5—2k). The fully protected inositol tetrakisphosphate 2i (390 mg, 0.29 mmol) was dissolved in 10 mL glacial acetic acid, and 1 g of 10% Pd/C was added. The mixture was hydrogenated at atmospheric pressure and room temperature for 3 h. After filtration, the solution was lyophilized to yield 2k as the free acid (183 mg, 98% yield) in form of a white powder; $^1$H NMR (DMSO-d₆, 200 MHz) δ(t, 3H, J=7 Hz), 0.94 (t, 3H, J=7 Hz), 1.53 (m, 2H), 1.63 (m, 2H), 2.38 (m,4H), 4.25–4.55 (m, 4H, H1,3,4,5), 5.20 (dd, 1H, J=9.0, 9.0 Hz, H6), 5.62 (m, 1H, H2); $^{31}$P NMR (DMSO-d₆, 121.5 MHz) δ+0.9, −0.1, −0.9, −1.4 (1:1:1:1); MS m/z (M-H)⁻ calcd 639.0046, obsd 639.0053.

Synthesis of 2,6-Di-O-Butyryl myo-Inositol 1,3,4,5-Tetrakisphosphate Octakis(acetoxymethyl)ester (Bt₂IP₄/AM, FIG. 5—2a). A solution of 2k (9.6 mg, 15 μmol) in 1 mL of dry CH₃CN was evaporated to dryness. DIEA (22 mg, 170 μmol) was added and again evaporated to dryness. Final dissolution of the salt in dry CH₃CN under argon was followed by addition of acetoxymethyl bromide (30 mg, 200 μmol) and more DIEA (23 mg, 180 μmol). The solution was stirred for 4 days and subsequently evaporated to dryness in high vacuum. The resulting oily mixture of salts was extracted with 1 mL of toluene to yield 12 mg (73%) of the desired octakis (acetoxymethyl) ester 2a in over 98% purity, determined by NMR. $^1$H NMR (toluene-d₈, 200 MHz) δ1.03 (t, 3H, J=7.5 Hz), 1.28 (t, 3H, J=7.5 Hz), 1.79 (m, 2H), 1.95–2.10 (8s+m, 26H, —CH₃ (AM), —CH₂— (but)), 2.29 (m,2H), 2.91 (dt, 2H, J=4.0, 7.5 Hz), 4.85 (ddd, 1H, J =9.3, 9.3, 9.3 Hz, H5), 4.90–5.08 (m, 2H, H1,3), 5.28 (ddd, 1H, J=9.5, 9.5, 9.5 Hz, H4), 5.60–6.15 (m, 17H, —CH₂—, H6), 6.37 (dd, 1H, J=3.0, 3.0 Hz, H2); $^{31}$P NMR (toluene-d₈, 121.5 MHz) δ−3.45, −3.80, −4.15 and −4.55 (1:1:1:1). MS m/z 1143 (M-CH₂OAc)⁻.

The strategies for the synthesis of the IP₃ and IP₄ hexakis- and octakis(acetoxymethyl)esters 1a and 2a are outlined in FIGS. 4 and 5 respectively, and were based on the use of tri- or dibutyryl esters of myo-inositol to mask the hydroxyl groups not to be phosphorylated. These esters increase solubility in organic solvents and permeability across membranes, prevent migration of phosphate from one hydroxyl to another, yet should be hydrolyzable in the cytosol. Because the L-enantiomers of IP₃ and IP₄ are known to have negligible binding to the receptors for the biologically active D-isomers (26), syntheses of the racemic compounds were considered adequate for these initial experiments. The synthesis of 2,3,6-tri-O-butyryl IP₃ hexakis(acetoxymethyl) ester (Bt₃IP₃/AM) began from 1,4,5,6-tetra-O-benzyl myo-inositol (FIG. 4—1b). Butyrylation followed by hydrogenolysis of the benzyl groups yielded 2,3-di-O-butyryl myo-inositol (FIG. 4—1c). The numbering in the synthesis schemes have been given in terms of the stereochemistry of the biologically active series, with the understanding that the mirror image is also present. The introduction of the third butyryl group was performed by reaction with one equivalent of butyric anhydride in pyridine. The reaction showed significant regioselectivity (56, 52). Of the four possible products only three were formed under the reaction conditions. The mixture was separated by preparative reverse-phase HPLC with elution in the following order: 2,3,6-(1d, 23%), 2,3,5- (1e—not shown, 5%), and 1,2,3-tri-O-butyryl myo-inositol (1f—not shown, 50%). Structures of the three structural isomers were assigned by one- and two-dimensional NMR. Phosphitylation of 2,3,6-tri-O-butyryl myo-inositol 1d with dibenzyl N,N-diethylphosphoramidite (53) in the presence of tetrazole in CH₃CN, followed by oxidation with peracetic acid (30% in AcOH) at −40° C. gave the fully protected Ins(1,4,5)P₃ 1g in racemic form in 49% yield after preparative HPLC. Hydrogenolysis in acetic acid at room temperature and atmospheric pressure and subsequent lyophilization afforded the desired free acid 2,3,6-tri-O-butyryl myo-inositol 1,4,5-trisphosphate (1h) (yield 99%) as a white powder, whose structure was verified by one- and two-dimensional $^1$H NMR as well as $^{31}$P NMR. This free acid was esterified with AM groups by stirring for 2 days with an excess of diisopropylethylamine (DIEA) and acetoxymethyl bromide (AM-Br) to yield 33% of sufficiently pure Bt₃IP₃/AM (1a).

In summary, the synthesis (FIG. 5) of 2,6-di-O-butyryl myo-inositol 1,3,4,5-tetrakisphosphate octakis (acetoxymethyl)ester ($Bt_2IP_4/AM$, 2a) began from myo-inositol 1,3,5-orthoformate(57)(2b). The 4-OH group was regioselectively benzylated in 86% yield as described e.g. by Billington et al (53). Subsequent butyrylation gave the crystalline 4-O-benzyl 2,6-di-O-butyryl myo-inositol 1,3,5-orthoformate (2d) in good yield. The hydrolysis of the orthoester 2d was performed in 80% $CF_3COOH$; monitoring by HPLC showed that the desired product 4-O-benzyl 2,6-di-O-butyryl myo-inositol (2e) reached a maximum after 7 h at room temperature. Isolation by preparative HPLC gave a 56% yield. The minor byproducts 4-O-benzyl 2-O-butyryl myo-inositol (2f) and 4-O-benzyl-6-O-butyryl myo-inositol (2g) could be isolated as a mixture from which 2f crystallized (5% yield). After hydrogenolysis of the benzyl group, the inositol dibutyrate 2h was phosphitylated as described for the synthesis of 1g. Oxidation and purification on preparative HPLC yielded the fully protected Ins(1,3,4,5)$P_4$ derivative 2i (yield 70%), which was hydrogenated to give 2,6-di-O-butyryl myo-inositol 1,3,4,5-tetrakisphosphate (2k, yield >99%, free acid) as a white powder after freeze-drying. 2k was reacted with an excess of DIEA and AM-Br in the usual way. The reaction mixture was evaporated to dryness and $Bt_2IP_4/AM$ (2a) was extracted with toluene in 76% yield. The NMR spectrum indicated that the product was sufficiently pure (>98%) to be used for biochemical purposes.

Figure 6A:
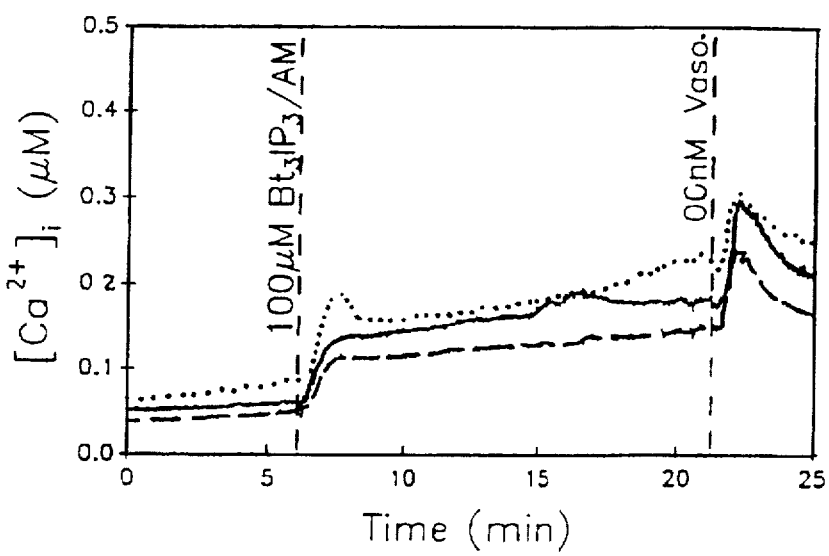
FIGS. 6A–6F depict test results which demonstrate the biological activity of $Bt_3IP_3/AM$ after it has traversed the cell membrane and undergone hydrolysis.
Figure 6B:
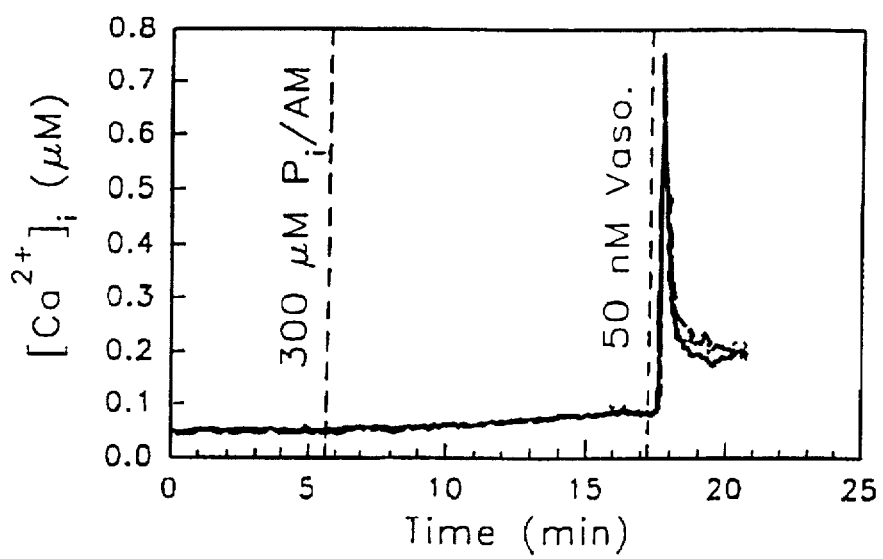

Biological Application of $Bt_3IP_3/AM$. The best-established biological effect of $IP_3$ is to release $Ca^{2+}$ from internal stores (26), so $Bt_3IP_3/AM$ (1a) was tested by imaging cytosolic free $Ca^{2+}$ levels in single REF-52 fibroblasts using standard methodology (58). Cells were loaded with the $Ca^{2+}$-indicator fura-2 and viewed by fluorescence excitation ratioing. $Bt_3IP_3/AM$ (100 μM) was applied extracellularly while monitoring cytosolic $Ca^{2+}$ concentrations. As shown in FIG. 6A, the $Ca^{2+}$ concentration increased to a new steady level within 2 minutes after addition of $Bt_3IP_3/AM$. The elevation of cytosolic $Ca^{2+}$ was well maintained, which shows that $IP_3$ and its metabolites are together sufficient to stimulate a continuing influx of extracellular $Ca^{2+}$ as well as release intracellular stores. Subsequent addition of vasopressin, a well-known $Ca^{2+}$-releasing hormone (59) had much less effect than normal (See FIG. 6B). This occlusion demonstrates that $Bt_3IP_3/AM$ had already saturated the same pathways to elevate $C^{2+}$ as utilized by a physiological agonist, vasopressin. Another example, shown in FIG. 6C, confirmed this: thapsigargin, a tumor promoter known to empty the $IP_3$-sensitive $Ca^{2+}$-stores (59,60) had no effect when applied after $Bt_3IP_3/AM$. The appearance of the traces was practically unchanged when the order of application was reversed (data not shown).

Figure 6C:
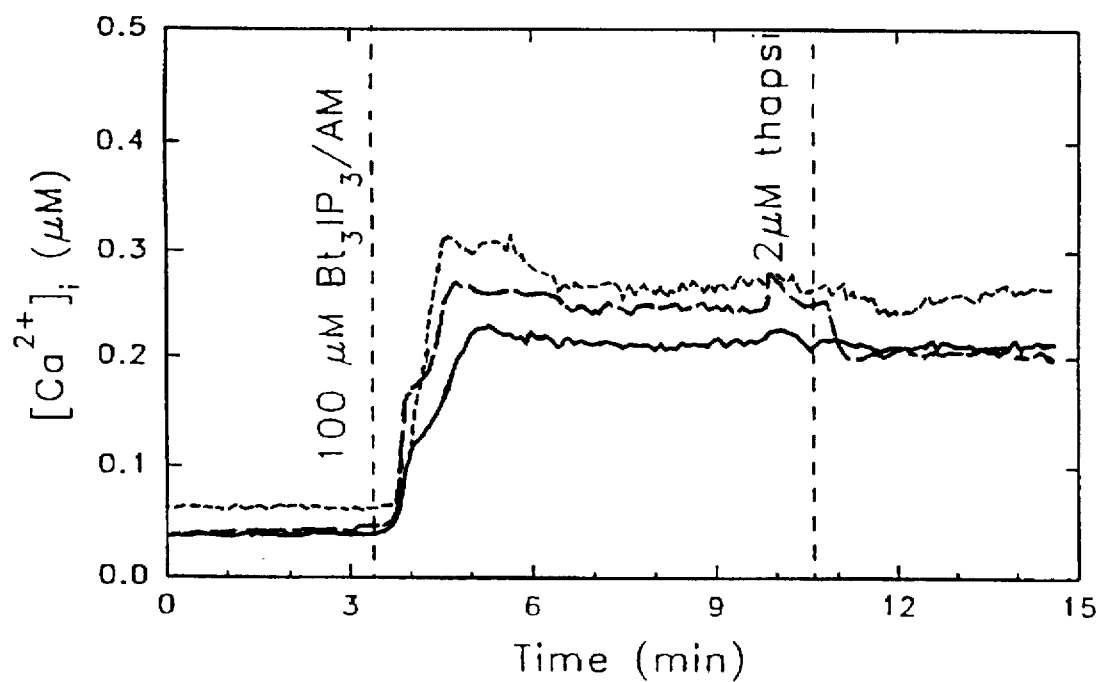
Figure 6D:
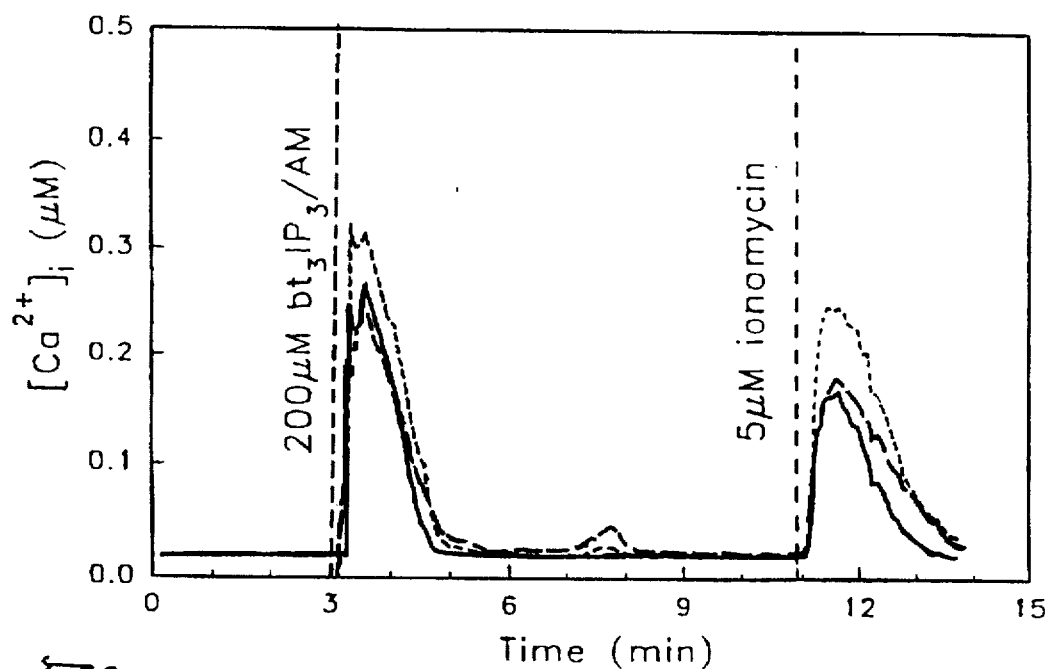

To further demonstrate that the above described plateau in the $Ca^{2+}$ levels after treatment with $Bt_3IP_3/AM$ is due to $Ca^{2+}$ influx, tests were performed in nominally $Ca^{2+}$-free medium containing 2 mM EGTA (FIG. 4D). Under these conditions $Bt_3IP_3/AM$ in some cases caused a brief $Ca^{2+}$ transient, indicating that the initial component is due to internal release, while the sustained plateau shown in FIGS. 6A and 6C represents $Ca^{2+}$ influx. These results strongly indicate that $Bt_3IP_3/AM$ is able to traverse the cell membrane, undergo sufficient hydrolysis to become biologically effective and release $Ca^{2+}$ from $IP_3$-sensitive stores.

Figure 6E:
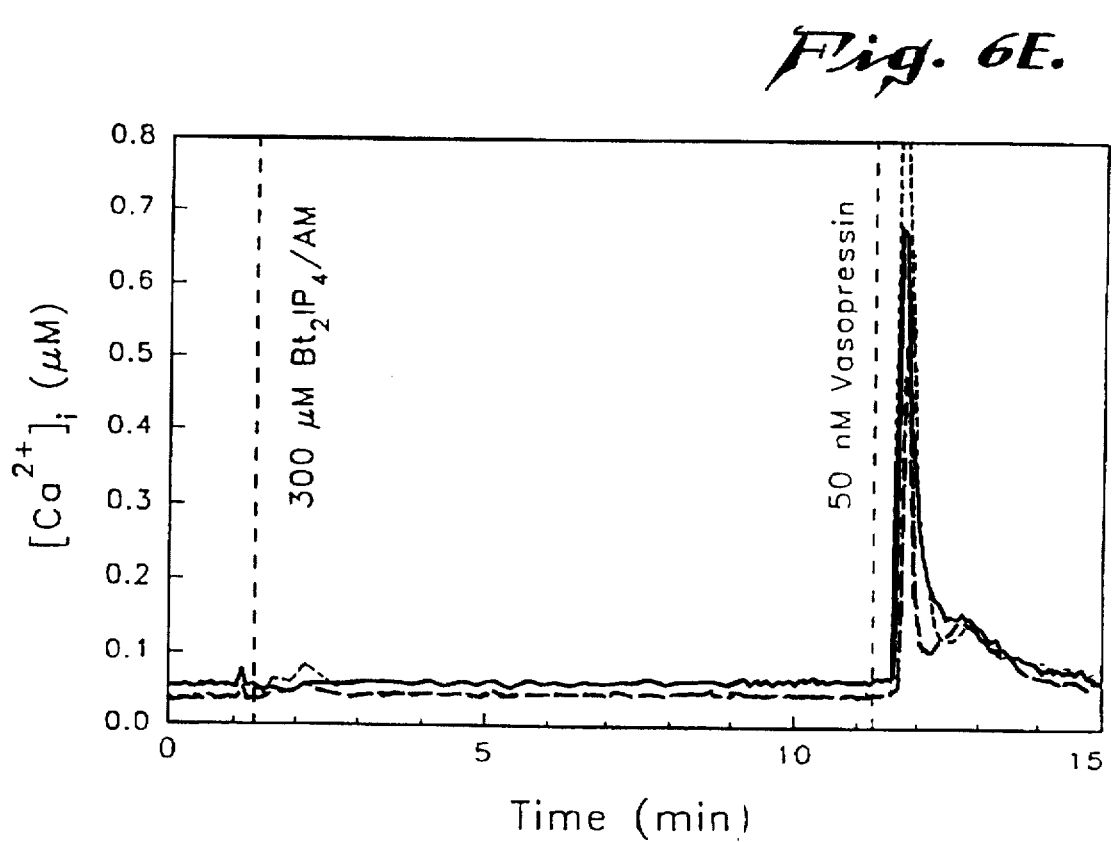
Figure 6F:
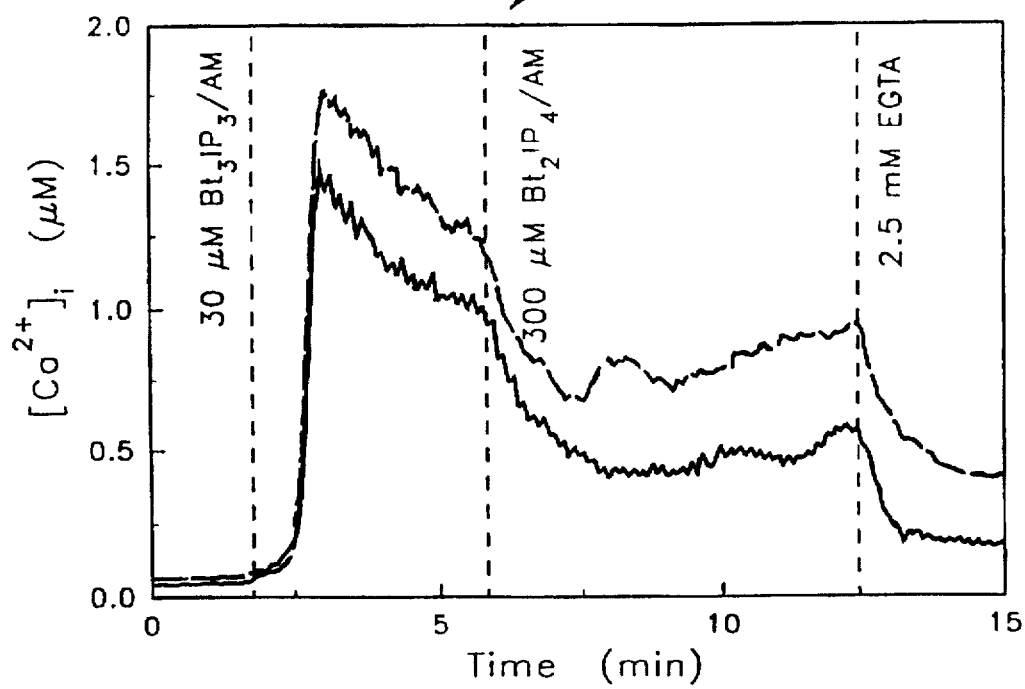

To control for nonspecific effects of AM ester hydrolysis, REF-52 cells were treated with 300 μM phosphate tris (acetoxymethyl)ester ($P_i$/AM) (15). Neither that compound nor $Bt_2IP_4/AM$ produced any significant change in the $Ca^{2+}$ levels (See FIGS. 6B, 6E). However, $Bt_2IP_4/AM$ (300 μM) applied after $Bt_3IP_3/AM$, at times when the $[Ca^{2+}]_i$ was high, caused a decrease in $[Ca^{2+}]_i$ in 5 of 13 cells (FIG. 6F). The remainder showed negligible alterations in $[Ca^{2+}]_i$ (data not shown).

It should be noted that there was significant variability between different batches of cells in the amplitudes of their $[Ca^{2+}]_i$ transients due to release of internal stores, whereas the amplitude due to sustained influx showed lesser but still significant variability. Cells may well vary in their ratio of esterase vs. $IP_3$-metabolizing activities, so that both the rate of increase and final level of effective $IP_3$ may similarly vary. Also, it was noticed that the $Bt_3IP_3/AM$ seemed most effective if mixed from a $Me_2SO$ stock solution into the buffer less than a minute before application to the cells. The apparent potency declined when the ester was diluted in buffer hours or more in advance or when aqueous solutions were frozen and thawed. This deterioration could reflect hydrolysis of the ester groups or adsorption to the walls of the plastic containers.

Figure 7:
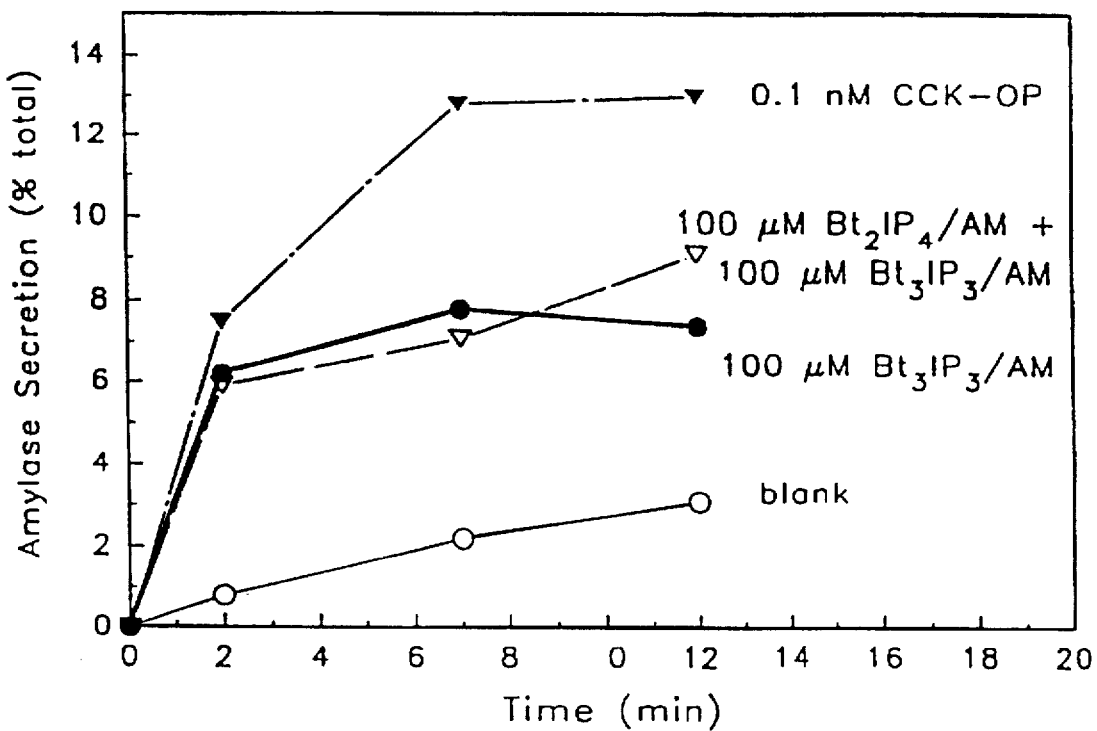
FIG. 7 depicts test results showing that $Bt_3IP_3/AM$ causes amylase secretion in pancreatic acinar cells.

To test whether these inositol phosphate derivatives could produce a complete physiological response not just a change in another intracellular messenger, we turned to pancreatic acinar cells. Various pancreatic secretagogues like cholecystokinin-octapeptide (CCK-OP), carbachol, and bombesin are known to stimulate amylase secretion mediated by $IP_3$ formation and rapid increases of $[Ca^{2+}]_i$ (61). We examined the ability of $Bt_3IP_3/AM$ and $Bt_2IP_4/AM$ to mimic the effect of those extracellular agonists. Both inositol phosphate derivatives were added immediately before the incubation alone or in combination at a concentration of 100 μM each. The effects were compared to experiments performed with buffer (blank) or a dose of CCK-OP, 0.1 nM, that causes a maximal rate of secretion. As shown in FIG. 7, $Bt_3IP_3/AM$ caused significant amylase secretion within 2 minutes. Direct comparison with the release due to CCK-OP shows similar values at this time point, but longer incubations with $Bt_3IP_3/AM$ gave no further increase in amylase secretion, apart from the basal leakage of amylase also shown by the untreated acini. $Bt_2IP_4/AM$ was not only completely ineffective when applied alone (data not shown) but was also unable to increase the secretion due to $Bt_3IP_3/AM$. These results show that $Bt_3IP_3/AM$ can rapidly enter pancreatic acinar cells, that acetoxymethyl- and butyrate esters are cleaved to a sufficient extent to release $IP_3$ or an active derivative, and that the $[Ca^{2+}]_i$ is sufficiently elevated to produce the appropriate physiological response. $Bt_2IP_4/AM$ does not seem to stimulate secretion on its own or modify that due to $Bt_3IP_3/AM$.

The above biological results show that neutral, hydrophobic, membrane-permeant derivatives of inositol phosphates can be synthesized and show the expected biological activity when applied extracellularly to intact REF-52 fibroblasts and pancreatic acinar cells. $Bt_3IP_3/AM$ released $Ca^{2+}$ from internal stores, as would be expected for an agent that mimicked $IP_3$. The peak height of the $[Ca^{2+}]_i$ transient was variable, often not as high as can be produced by a sudden high dose of an agonist such as vasopressin that activates endogenous $IP_3$ production (62). In some cases lower doses of $Bt_3IP_3/AM$ gave peak $[Ca^{2+}]_i$ over 1 μM. A reasonable explanation is the $Bt_3IP_3/AM$ has to undergo hydrolysis of up to nine protecting groups (three butyryl and six acetoxymethyls), so that the concentration of the active species probably rises not as a step function or spike but rather with a ramp-like or sigmoidal time course. Therefore the $Ca^{2+}$ should trickle out relatively gradually, allowing buffering, sequestration, and extrusion mechanisms more time to blunt the peak $[Ca^{2+}]_i$. Also, a gradual rise in $IP_3$ and $[Ca^{2+}]_i$ may fail to recruit the positive feedback due to transient $Ca^{2+}$-stimulation of the $IP_3$ receptor, but would still activate the slower negative feedback $Ca^{2+}$-inactivation (63).

Permeant inositol polyphosphate derivatives as described above are useful to investigate longer-term effects on cells not mediated through cytosolic $[C^{2+}]_i$. For example, possible effects on protein synthesis, phosphorylation, proliferation (49), or gene expression are relatively difficult to study on microinjected, patch-clamped, or permeabilized cells.

Figure 8:
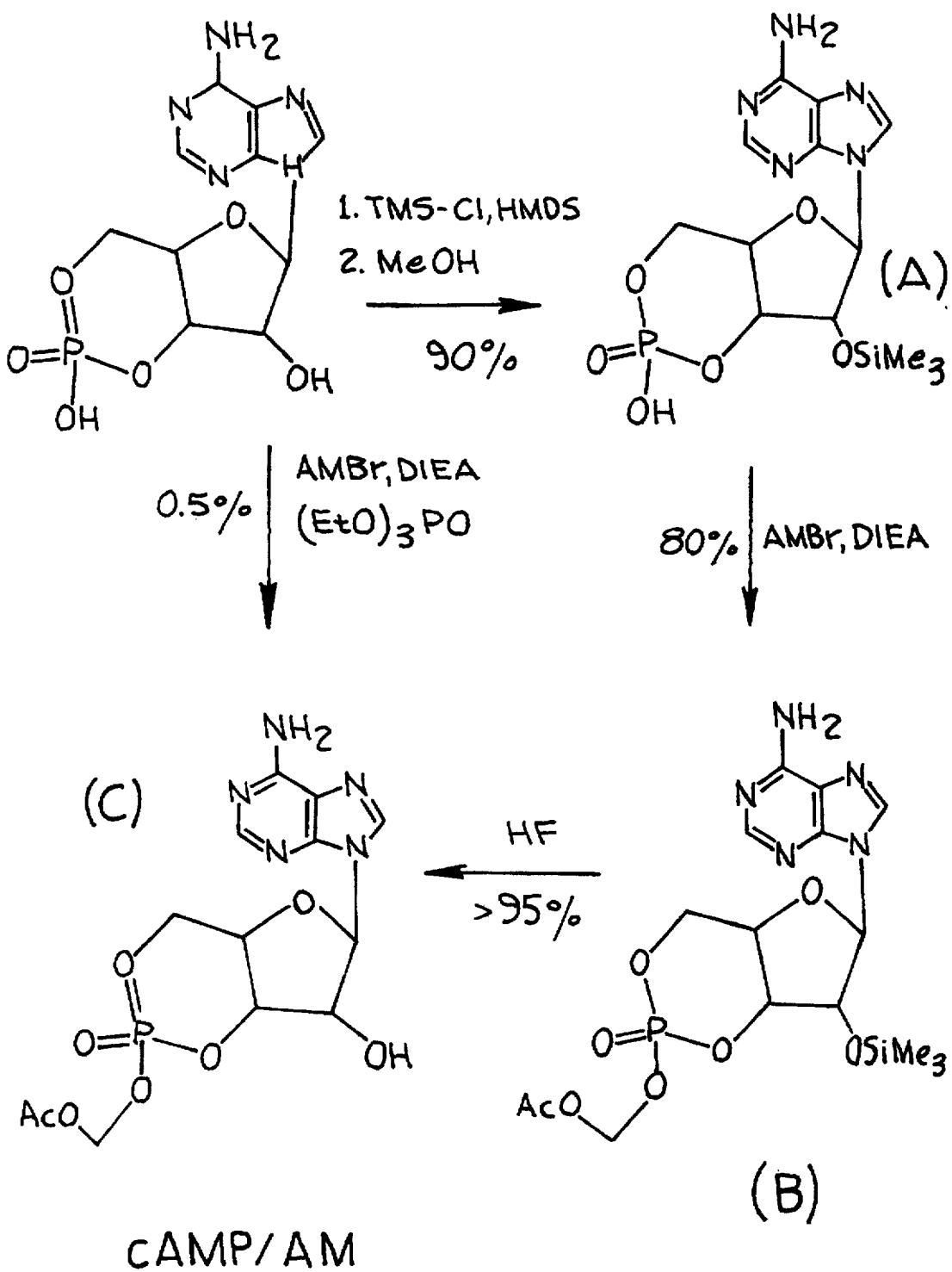
FIG. 8 depicts the synthesis scheme preparing 3', 5'-cyclic monophosphate acetoxymethyl ester.

The synthesis of cAMP and cGMP described above utilizes butyryl groups to mask or protect the hydroxyl groups. This is because the direct conversion of a cAMP or cGMP into their acetoxy esters yields only minute amounts of product. Trimethyl-silyl (TMS) groups were also found to work well as a protective group. The synthesis schemes for direct and TMS protected synthesis is shown in FIG. 8.

Synthesis of the acetoxy ester of cAMP using TMS is set forth below:

General Methods—Proton and $^{31}P$ NMR spectra were obtained in $CDCl_3$ with residual $CHCl_3$ ($\delta$=7.26), being used as the internal standard for $^1H$ spectra. 85% phosphoric acid was used as an external standard for $^{31}P$ spectra. All NMR spectra were recorded on either a Varian Gemini-200 (200 MHz) or a General Electric QE-300 (300 MHz) spectrometer and are reported with the same abbreviations as in the preceding examples.

Acetonitrile were stored over activated molecular sieve (3 Å) for at least 3 d. All other solvents were purchased in highest purity available and were used as received. N,N-Diisopropylethylamine (DIEA) was distilled from $CaH_2$. Acetoxymethyl bromide (AM-Br) was prepared according to known procedures. cGMP was from ICN or Calbiochem. All other nucleotides were from Sigma. All other reagents were from Aldrich.

The following three step synthesis is outlined in FIG. 8.

Synthesis of 2'-O-Trimethylsilyl Adenosine 3',5'-cyclic phosphate (FIG. 8—A)—The free acid of cAMP (50 mg, 0.15 mmol) was suspended in 3 mL dry DIEA. 1 mL Hexamethyldisilazane (HMDS) and 0.5 mL Trimethylsilyl chloride (TMS-Cl) were added under Ar and the mixture was heated to 100° C. for 3 h. After cooling to r.t. all volatile components were evaporated off in high vacuum. The residual oil was extracted with 2×2 mL dry toluene. A sample of the extract, exclusively containing $N^6$, 2'-O-di (trimethylsilyl) adenosine 3',5'-cyclic monophosphate trimethylsilyl ester, was evaporated to dryness and analyzed by NMR: $^1H$ NMR (toluene-$d_8$, 200 MHz) diastereomere 1 (80%) $\delta$0.32 (s, 9H), 0.45 (s, 9H), 0.47 (s, 9H), 4.15–4.6 (m, 3H, H4', H5'$_{eq}$, H5'$_{ax}$), 4.98 (d, 1H, J=4.7 Hz, H2'), 5.60 (s, 1H, $N^6$H), 5.74 (ddd, 1H, J=1.6, 4.7, 9.5 Hz, H3'), 5.83 s, 1H, H1', 7.64 (s, 1H, H2), 8.6 (s, 1H, H8). Diastereomere 2 (20%) $\delta$4.65 (d, 1H, J=4.2 Hz, H2'), 5.20 (m, 1H, H3'), 5.66 (s, 1H, $N^6$H), 6.05 (s, 1H, H1'), 7.77 (s, 1H, H2), 8.58 (s, 1H, H8). The toluene extract was treated with 12 µL MeOH (0.3 mmol) for 3 min. followed by rapid evaporation of the solvents. The remaining white solid fairly pure 2'-O-TMS-cAMP (1). $^1H$ NMR (CD, OD, 200 MHz) $\delta$0.80 (s, 9H, TMS), 4.32 (m, 3H, H4', H5'), 4.65 (d, 1H, J=8.2 Hz, H2'), 4.95 (m, 1H H3'), 6.12 (s, 1H, H1'), 7.16 (broad s, 2H, $NH_2$), 8.40, 8.45 (2s, 1H each, H2, H8). $^{31}$H-NMR O.

Synthesis of 2'-O-Trimethylsilyl Adenosine 3',5'-cyclic Monophosphate Acetoxymethyl Ester (FIG. 8—B)—25 mg (0.062 mmol) 2'-TMS-cAMP (1) was dissolved in 0.5 mL dry $CH_3CN$ containing 0.05 mL DIEA (0.28 mmol) under Ar and 0.028 mL (0.28 mmol) AMBr were added. The mixture was stirred for 3 days at r.t. then evaporated to dryness. The crude produce was purified on a Si60 column (4×1.5 cm) with dry $CH_3CN$ saturated with hexane as the eluent. Prior to the separation the column was washed with the same eluent containing 0.1% acetic acid followed by the eluent alone. Most of the 2'-O-TMS-cAMP/AM (2) eluated just before HDIEA$^+$Br to yield 20.5 mg (0.042 mmol, 68%). The product consisted of 90% of one of the $R_P/S_P$-diastereomeres, as determined by $^{31}P$ NMR. $^1H$ NMR ($CDCl_3$, 300 MHz) $\delta$0.22 (s, 9H, TMS), 2.16 (s, 3H, —$OCCH_3$), 4.43 (m, 2H, H4', H5'), 4.64 (m, 1H, H5'$_{eq}$), 4.85 (d, 1H, J=5.2 Hz, H2'), 5.34 (m, 1H, H3'), 5.74 (d, 2H, J=13.1 Hz, —$CH_2$—OAc), 4.86 (broad s, 2H, $NH_2$), 5.91 (s, 1H, H1'), 7.87 and 8.41 (2s, 1H each, H2 and H8). $^{31}P$ NMR ($CDCl_3$, 121.5 Hz) $\delta$–7.58 (90%), –4.62 (10%).

Synthesis of Adenosine 3',5'-cyclic Monophosphate Acetoxymethyl Ester (FIG. 8—C)—14 mg (0.029 mmol) of 2 were dissolved in 1 mL of a 1:1 (v/v0 mixture of $CHCl_3/CH_3CN$ and 2 µL HF (49%) was added. The mixture was gently swirled for 2 min. before the solvents were evaporated off to quantitatively yield cAMP/AM (3) as a white solid. $^1H$ NMR ($CD_3OD$, 300 MHz) $\delta$2.17 (s, 3H, OAc), 4.48 (ddd, 1H, J=3.6, 9.5, 9.5 Hz, H4'), 4.50 (m, 1H, H5'$_{ax}$), 4.74 (m, 1H, H5'$_{eq}$), 5.33 (ddd, 1H, J=1.0, 4.8, 12.3 Hz, H3'), 5.75 (m, 2H, —$CH_2$—OAc), 6.15 (s, 1H, H1'), 8.41 and 8.42 (2s, 1H each, H2, H8). $^{31}P$ NMR ($CD_3OD$, 121.5 MHz)$\delta$–6.85.

Figure 9:
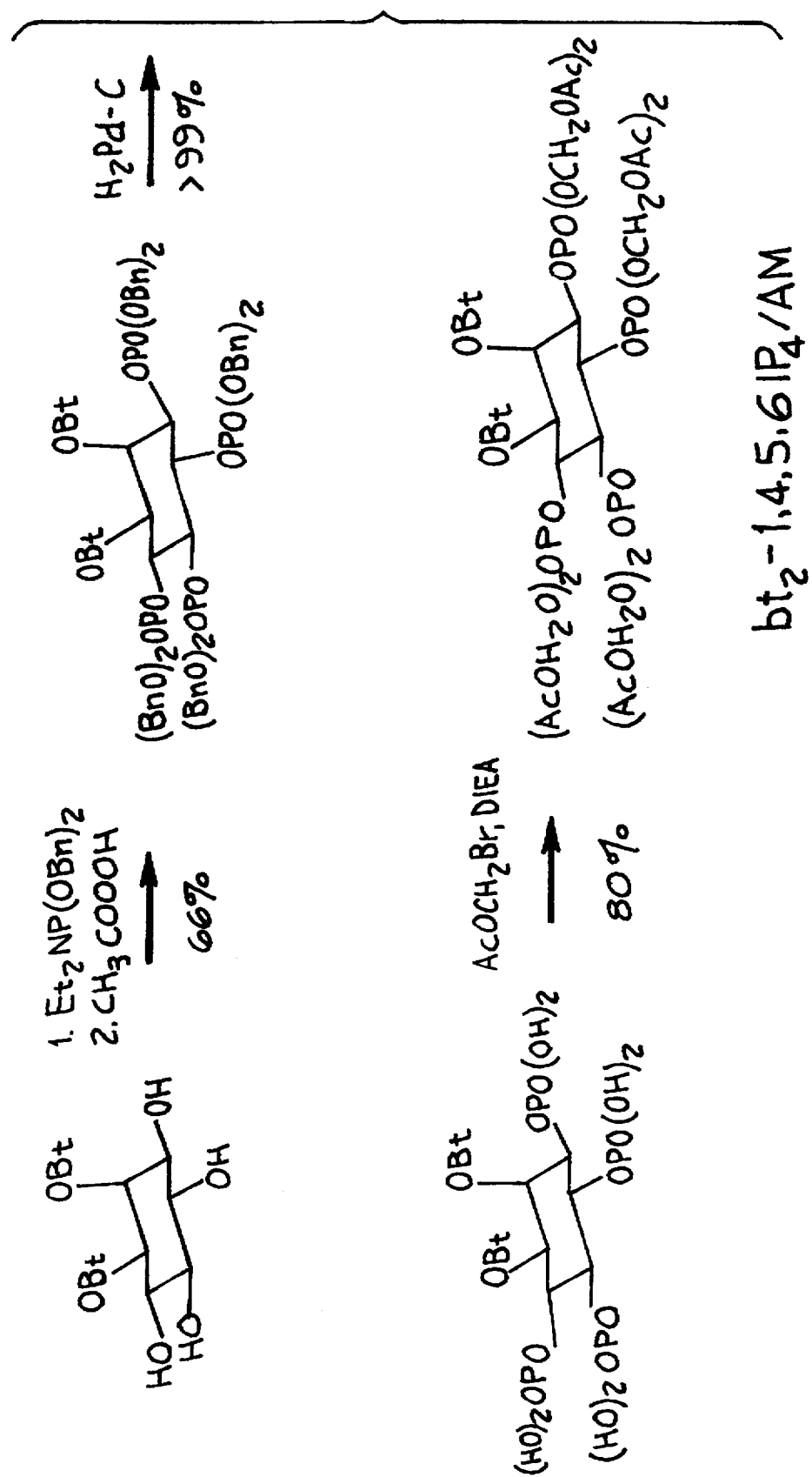
FIG. 9 shows the synthesis scheme for preparing 2,3-Di-O-butyryl myo-inositol 1,4,5,6-tetrakis phosphate octakis (acetoxymethyl) ester.

Another example involves the synthesis of 2,3-Di-O-butyryl myo-inositol 1,4,5,6-Tetrakisphosphate octakis (acetoxymethyl)ester (bt$_2$-1,4,5,6-IP$_4$/AM). The synthesis starts from 2,3-di-O-butyryl myo-inositol (previously described). The procedure closely follows the synthesis pathway 2h→2i→2k→2 (see FIG. 5). A schematic representation of the synthesis pathway is shown in FIG. 9.

Having thus described exemplary embodiments of the present invention, it will be understood by those skilled in the art that the within disclosures are exemplary only and that the invention is only limited by the following claims.

BIBLIOGRAPHY

1. Hardie, D. G. (1991) *Biochemical Messengers: Hormones, Neurotransmitters and Growth Factors.* Champman & Hall, London 2. Robinson, G. A., Butcher, R. W., and Sutherland, E. W. (1971) *Cyclic AMP.* Academic Press, New York 3. Corbin, J. D., Johnson, R. A., eds (1988) *Methods in Enzymology: Initiation and Termination of Cyclic Nucleotide Action.* Academic Press, Inc., San Diego 4. Goy, M. F.(1991) *Trends Neurosci.* 14, 293–299

5. Berridge, M. J. and Irvine, R. F. (1989) *Nature* 341, 197–205

6. Meyer, R. B., Jr. (1980) in *Burger's Medicinal Chemistry* (Wolff, M. E., ed) pp. 1201–1224, Wiley, New York 7. Polokoff, M. A., Bencen, G. H., Vacca, J. P., deSolms, S. J., Young, S. D., and Huff, J. R. (1988) *J. Biol. Chem.* 263, 11922–11927

8. Henion, W. F., Sutherland, E. W., and Posternak, T. (1967) *Biochim. Biophys. Acta* 148, 106–113

9. Roche, E. B., ed (1987) *Bioreversible Carriers in Drug Design* Pergamon Press, New York 10. Falbriard, J. -G., Posternak, T., and Sutherland, E. W. (1967) *Biochim. Biophys. Acta* 148, 99–105

11. Jansen, A. B. A. and Russell, T. J. (1965) *J. Chem. Soc.* 2127–2132
12. Tsien, R. Y. (1981) *Nature* 290, 527–528
13. Grynkiewicz, G., Poehie, M., and Tsien, R. Y. (1985) *J. Biol. Chem.* 260, 3440–3450
14. Tsien, R. Y. (1989) *Methods Cell Biol.* 30, 127–156
15. Srivastva, D. N. and Farquhar, D. (1984) *Bioorg. Chem.* 12, 118–129
16. Iyer, R. P., Phillips, L. R., Biddle, J. A., Thakker, D. R., Egan, W., Aoki, S., and Mitsuga, H. (1989) *Tetrahedron Lett.* 30, 7141–7144
17. Sastry, J. K., Nehete, P. N., Khan, S., Nowak, B. J., Plunkett, W., Arlinghaus, R. B., and Farquhar, D. (1992) *Mol. Pharmacol.* 41, 441–445
18. Freed, J. J., Farquhar, D., and Hompton, A. (1989) *Biochem. Pharmacol.* 38, 3193–3198
19. Saperstein, R., Vicario, P. P., Strout, H. V., Brady, E., Slater, E. E., Greenlee, W. J., Ondeyka, D. L., Patchett, A. A., and Hangauer, D. G. (1989) *Biochemistry* 28, 5694–5701
20. Walker, J. W., Reid, G. P., McCray, J. A., and Trentham, D. R. (1988) *J. Am. Chem. Soc.* 110, 7170–7177
21. Nerbonne, J. M., Richard, S., Nargeot, J., and Lester, H. A. (1984) *Nature* 310, 74–76
22. Engels, J. and Schlaeger, E. -J. (1977) *J. Med. Chem.* 20, 907–911
23. Walker, J. W., Feeney, J., and Trentham, D. R. (1989) *Biochemistry* 28, 3272–3280
24. Gurney, A. M. and Lester, H. A. (1987) *Physiol. Rev.* 67, 583–617
25. McCray, J. A. and Trentham, D. R. (1989) *Annu. Rev. Biophys. Biophys. Chem.* 18, 239–270
26. Berridge, M. J. and Irvine, R. F. (1989) *Nature* 341, 197–205
27. Irvine, R. F. and Moor, R. M. (1986) *Biochem. J.* 240, 917–920
28. Irvine, R. F. (1990) *FEBS Letters* 263, 5–9
29. Morris, A. P., Gallacher, D. V., Irvine, R. F., and Petersen, O. H. (1987) *Nature* 330, 653–655
30. Changya, L., Gallacher, D. V., Irvine, R. F., Potter, B. V. L., and Petersen, O.H. (1989) *J. Membrane Biol.* 109, 85–93
31. Boynton, A. L., Dean, N. M., and Hill, T. D. (1990) *Biochem. Pharmacol.* 40, 1933–1939
32. Hill, T. D., Dean, N. M., and Boynton, A. L. (1988) *Science* 242, 1176–1178
33. Crossley, I., Swann, K., Chambers, E., and Whitaker, M. (1988) *Biochem. J.* 252, 257–262
34. Snyder, P. M., Krause, K. -H., and Welsh, M. J. (1988) *J. Biol. Chem.* 263, 11048–11051
35. Tsien, R. W. and Tsien, R. Y. (1990) *Annu. Rev. Cell Biol.* 6, 715–760
36. Bird, G. St J., Rossier, M. F., Hughes, A. R., Shears, S. B., Armstrong, D. L., and Putney, J. W. jr. (1991) *Nature* 352, 162–165
37. Balla, T., Sim, S. S., Iida, T., Choi, K. Y., Catt, K. J., and Rhee, S. G. (1991) *J. Biol. Chem.* 266, 24719–24726
38. Grynkiewicz, G. and Tsien, R. Y. (1987) *Pol. J. Chem.* 61, 443–447
39. Adams, S. R., Harootunian, A. T., Buechler, Y. J., Taylor, S. S., and Tsien, R. Y. (1991) *Nature* 349, 694–697
40. Dharmsathaporn, K., Mandel, K. G., Masui, H., and McRoberts, J. A. (1985) *J. Clin. Invest.* 75, 462–470
b 41. Madara, J. and Dharmsathaporn, K. (1985) *J. Cell Biol.* 101, 2124–2133
42. Dharmsathaporn, K., Mandel, K. G., McRoberts, J. A., Tisdale, L. D., and Masui, H. (1984) *Am. J. Physiol.* 264, G204–G208
43. McRoberts, J. A. and Barrett, K. E. (1989) *Modern Cell Biology* (Mathi, K. S. and Valeulich, J. D., eds) pp. 235–265, Alan R. Liss, Inc., New York
44. Sammak, P. J., Adams, S. R., Harootunian, A. T., Schliwa, M., and Tsien, R. Y. (1992) *J. Cell Biol.* 117, 57–72
45. Taylor, S. S., Buechler, J. A., and Yonemoto, W. (1990) *Annu. Rev. Biochem.* 59, 971–1005
46. Barrett, K. E. and Dharmsathaporn, K. (1991) *Textbook of Gastroenterology* (Yamada, T., ed) pp. 265–294, J.B. Lippincott Co., Philadelphia
47. Schliwa, M. (1975) *Microtubules and Microtubule Inhibitors* (Borgers, M. and de Brabender, M., eds) pp. 215–228, Elsevier Science, Amsterdam
48. Beebe, S. J., Blackmore, P. F., Chrisman, T. D., and Corbin, J. D. (1988) *Methods Enzymol.* 159, 118–139
49. Smirnova, L. I., Malenkovskaya, N. A, Preddoditelev, D. A., and Nifant'ev, E. E. (1980) *Zh. Org. Khim.* 16, 1011–1019
50. Angyal, S. J. and Tate, M. E. (1965) *J. Chem. Soc.* 6949–6955
51. Tegge, W. (1986) *Ph.D. Thesis* University of Bremen-FRG
52. Lee, H. W. and Kishi, Y. (1985) *J. Org. Chem.* 50, 4402–4404
53. Billington, D. C., Baker, R., Kulagowski, J. J., Mawer, I. M., Vacca, J. P., deSolms, S. J., and Hugg, J. R. (1989) *J. Chem. Soc. Perkin Trans.* 1 1423–1429
54. Baudin, G., Glanzer, B. I., Swaminathan, K. S., and Vasella, A. (1988) *Helv. Chim. Acta* 71, 1367–1378
55. Tegge, W. and Ballou, C. E. (1989) *Proc. Natl. Acad. Sci. USA* 86, 94–98
56. Perich, J. W. and Johns, R. B. (1987) *Tetrahedron Lett.* 28, 101–102
57. Thastrup, O., Cullen, P. J., Drobak, B. K., Hanley, M. R., and Dawson, A. P. (1990) *Proc. Natl. Acad. Sci. USA* 87, No. 7, 2466–2470
58. Tsien, R. Y. and Harootunian, A. T. (1990) *Cell Calcium* 11, 93–109
59. Harootunian, A. T., Kao, J. P. Y., Paranjape, S., Adams, S. R., Potter, B. V. L., and Tsien, R. Y. (1991) *Cell Calcium* 12, 153–164
60. Harootunian, A. T., Kao, J. P. Y., Paranjape, S., and Tsien, R. Y. (1991) *Science* 251, 75–78
61. Finch, E. A., Turner, T. J., and Goldin, S. M. (1991) *Scient* 252, 443–446
62. Kuno, M. and Gardner, P. (1987) *Nature* 236, 301–304
63. Penner, R., Matthews, G., and Neher, E. (1988) *Nature* 334, 499–504
64. Schultz, C. et al. (1993) *Journal of Biological Chemistry* Vol. 268, No. 9, 6316–6322

What is claimed is:

1. A method for introducing cAMP or cGMP into a cell in vitro without disrupting the cell membrane, said method comprising the steps of:

esterifying the phosphate group present in said cAMP or cGMP to form an acetoxyalkl ester of said cAMP or cGMP wherein the alkyl group of said ester has from 1 to 7 carbon atoms and the acetyl group is located at the 1 position of said alkyl group;

introducing said acetoxyalkyl ester of cAMP or cGMP into said cell without disrupting said cell membrane; and allowing the cell to cleave the acetoxyalkyl ester to form cAMP or cGMP within said cell.

2. A method according to claim 1 which includes the additional step of masking the hydroxyl groups present in cAMP or cGMP prior to introduction into said cell with one or more acyl groups having from 1 to 4 carbon atoms.

3. A method according to claim 2 wherein said acyl groups are butyryl.

4. A composition of matter comprising the acetoxyalkyl ester of 8-substituted cAMP or cGMP wherein the alkyl group of said ester has from 1 to 7 carbon atoms and the acetyl group is located at the 1 position of said alkyl group.

5. A composition of matter according to claim 4 wherein said 8-substituted cAMP or cGMP is 8-bromo-cAMP or 8-bromo-cGMP.

6. A composition of matter according to claim 4 wherein said 8-substituted cAMP or cGMP is 8-chloro-cAMP or 8-chloro-cGMP.

7. A composition of matter according to claim 4 wherein said 8-substituted-cAMP or cGMP is 8-(p-chlorophenylthio)-cAMP or 8-(p-chlorophenylthio)-cGMP.

8. A method for introducing 8-substituted cAMP or cGMP into a cell in vitro without disrupting the cell membrane, said method comprising the steps of:

esterifying the phosphate group present in said 8-substituted cAMP or cGMP to form an acetoxyalkyl ester of said 8-substituted cAMP or cGMP wherein the alkyl group of said ester has from 1 to 7 carbon atoms and the acetyl group is located at the 1 position of said alkyl group;

introducing said acetoxyalkyl ester of said 8-substituted cAMP or cGMP into said cell without disrupting said cell membrane; and allowing the cell to cleave said acetoxyalkyl ester to form said phosphate-containing 8-substituted cAMP or cGMP within said cell.

9. A method for introducing cAMP or cGMP into a cell in vitro according to claim 1 wherein said acyloxyalkyl ester of cAMP or cGMP is an acetoxy methyl ester.

10. A method for introducing cAMP or cGMP into a cell in vitro according to claim 1 wherein said acyloxyalkyl ester of cAMP or cGMP is an acetoxy methyl ester.

* * * * *